United States Patent
Robert et al.

(10) Patent No.: US 10,995,351 B1
(45) Date of Patent: May 4, 2021

(54) SYSTEM AND METHOD FOR PRODUCING A CARBOHYDRATE STREAM FROM A CELLULOSIC FEEDSTOCK

(71) Applicant: Fluid Quip Technologies, LLC, Springfield, OH (US)

(72) Inventors: Jeffrey P Robert, Garden Valley, ID (US); Neal Jakel, Cedar Rapids, IA (US); Donald M. Cannon, Mount Vernon, IA (US)

(73) Assignee: Fluid Quip Technologies, LLC, Springfield, OH (US)

( * ) Notice: Subject to any disclaimer, the term of this patent is extended or adjusted under 35 U.S.C. 154(b) by 0 days.

(21) Appl. No.: 17/019,696

(22) Filed: Sep. 14, 2020

(51) Int. Cl.
*C12P 19/14* (2006.01)
*C12P 19/02* (2006.01)
*C13K 1/02* (2006.01)

(52) U.S. Cl.
CPC ............... *C12P 19/02* (2013.01); *C13K 1/02* (2013.01)

(58) Field of Classification Search
CPC ...................... C12P 19/14; C12P 19/02
See application file for complete search history.

(56) References Cited

U.S. PATENT DOCUMENTS

| | | | |
|---|---|---|---|
| 3,249,512 A | 5/1966 | Bode | |
| 4,330,625 A | 5/1982 | Miller et al. | |
| 4,361,651 A | 11/1982 | Keim | |
| 4,407,955 A | 10/1983 | Muller et al. | |
| 4,578,353 A | 3/1986 | Assarsson et al. | |
| 4,810,328 A | 3/1989 | Freis et al. | |
| 6,962,722 B2 | 11/2005 | Dawley et al. | |
| 7,452,425 B1 | 11/2008 | Langhauser | |
| 7,488,390 B2 | 2/2009 | Langhauser | |
| 7,494,675 B2 | 2/2009 | Abbas et al. | |
| 7,598,069 B2 | 10/2009 | Felby et al. | |
| 7,842,490 B2 | 11/2010 | Felby et al. | |
| 7,985,847 B2 | 7/2011 | Belanger et al. | |
| 8,278,080 B2 | 10/2012 | Yoon | |
| 8,557,540 B2 | 10/2013 | Burlew et al. | |
| 8,652,818 B2 | 2/2014 | Lawton, Jr. et al. | |
| 8,722,372 B2 | 5/2014 | Kiuchi et al. | |
| 8,778,433 B2 | 7/2014 | Lee | |
| 8,813,973 B2 | 8/2014 | Lee et al. | |
| 9,012,191 B2 | 4/2015 | Lee | |
| 9,068,205 B2 | 6/2015 | Purtle et al. | |
| 9,273,329 B2 | 3/2016 | Kusuda et al. | |
| 9,523,104 B2 | 12/2016 | Fuchs et al. | |
| 9,777,303 B2 * | 10/2017 | Jakel | C12P 7/10 |
| 9,909,158 B2 | 3/2018 | Yamada et al. | |
| 9,920,346 B2 | 3/2018 | Funada et al. | |
| 9,926,613 B2 | 3/2018 | Kishimoto et al. | |
| 10,119,157 B2 * | 11/2018 | Jakel | C13K 1/06 |
| 10,480,038 B2 * | 11/2019 | Jakel | A23L 7/104 |
| 2006/0083823 A1 | 4/2006 | Fox et al. | |
| 2006/0251762 A1 | 11/2006 | Jansen et al. | |
| 2007/0014905 A1 | 1/2007 | Chen et al. | |
| 2007/0020375 A1 | 1/2007 | Jansen et al. | |
| 2008/0260902 A1 | 10/2008 | Van Houten et al. | |
| 2009/0162892 A1 | 6/2009 | Pompejus et al. | |
| 2009/0238918 A1 | 9/2009 | Jansen et al. | |
| 2009/0258106 A1 | 10/2009 | Jansen et al. | |
| 2011/0236946 A1 | 9/2011 | Maclachlan et al. | |
| 2012/0244590 A1 | 9/2012 | Lee | |
| 2013/0065289 A1 | 3/2013 | Carlson | |
| 2013/0236936 A1 | 9/2013 | Lee | |
| 2013/0295661 A1 | 11/2013 | Roesch et al. | |
| 2014/0024064 A1 | 1/2014 | Burlew et al. | |
| 2014/0106419 A1 * | 4/2014 | Bazzana | C12P 7/16 435/134 |
| 2014/0193872 A1 | 7/2014 | Chen et al. | |
| 2014/0227757 A1 | 8/2014 | Jin et al. | |
| 2014/0234935 A1 | 8/2014 | Kusuda et al. | |
| 2014/0273127 A1 | 9/2014 | Fuchs et al. | |
| 2014/0287469 A1 | 9/2014 | Medoff et al. | |
| 2014/0356915 A1 | 12/2014 | Retsina et al. | |
| 2015/0004647 A1 | 1/2015 | Niwa et al. | |
| 2015/0284745 A1 | 10/2015 | Kozyuk et al. | |
| 2015/0344921 A1 | 12/2015 | Kacmar et al. | |
| 2016/0160242 A1 | 6/2016 | Mimitsuka et al. | |
| 2016/0186215 A1 | 6/2016 | Redford | |
| 2016/0289704 A1 | 10/2016 | Medoff | |
| 2016/0289705 A1 | 10/2016 | Medoff | |
| 2016/0289706 A1 | 10/2016 | Medoff | |
| 2016/0298141 A1 | 10/2016 | Medoff | |
| 2016/0298142 A1 | 10/2016 | Yu et al. | |
| 2016/0312258 A1 | 10/2016 | Ikeo et al. | |

FOREIGN PATENT DOCUMENTS

| | | |
|---|---|---|
| EP | 3121258 A1 | 1/2017 |
| WO | 2012075481 A1 | 6/2012 |
| WO | 2014150022 A1 | 9/2014 |
| WO | 2014182807 A1 | 11/2014 |

* cited by examiner

*Primary Examiner* — Tekchand Saidha
(74) *Attorney, Agent, or Firm* — Wood Herron & Evans LLP

(57) ABSTRACT

Systems and methods for producing carbohydrate (e.g., sugar) streams (and recycling enzymes) from a pretreated or untreated biomass such as cellulosic feedstock, including, for example, "brown stock" feedstock, or waste or recycled fiber sludge produced in the pulp and paper industry, such as for biochemical (e.g., biofuel) production, are provided. In one example, the system and method can produce high purity C6 (glucose and/or fructose) and/or C5 (xylose) sugar streams, and other carbohydrates and/or fibrous materials, from cellulosic feedstocks, such as brown stock or waste fiber sludge, that can be effectively converted into various biochemical products, such as ethanol.

20 Claims, 6 Drawing Sheets

SYSTEM AND METHOD FOR PRODUCING A CARBOHYDRATE STREAM FROM A CELLULOSIC FEEDSTOCK

TECHNICAL FIELD

The present invention relates generally to systems and methods for use in the biochemical industry such as the cellulosic and biofuel industries and, more specifically, to improved systems and methods that can utilize cellulosic feedstock for producing industrial carbohydrate streams (e.g., sugar streams, fiber streams, and the like), such as for biochemical (e.g., biofuel) production.

BACKGROUND

The cellulosic ethanol, advanced biofuels, and biochemical industries have been unable to meet commercialization expectations for many years due to prohibitive economics concerning capital and operational expenditures and due to technical challenges including pretreatment of cellulosic feedstocks required to produce carbon 5 and/or 6 (C5 and/or C6) sugars, and other carbohydrates and/or fibrous materials, which may be able to be converted into a bio-based (e.g., a biochemical) product. Typically, a cellulosic feedstock must be "pretreated" or conditioned prior to introducing the feedstock into an industrial sugar producing system. But again, the capital and/or operational expenditures, and technical challenges, oftentimes frustrate the cost-effectiveness of this approach compared to conventional grain-based sugar production methods.

Also, the pulp and paper industry, within the last two decades or so, has been challenged with economic adversity. The capital expenditures and the processes developed for production of virgin pulp, for example, do not necessarily provide the return on investment that would justify the original and ongoing expenditures required to run a paper-producing pulp operation. Such virgin pulp (and other types) could be a ripe source of C6/C5 cellulosic sugars for the bio-based or biochemical industry, such as the cellulosic ethanol and biofuels industries.

Yet further, pulp and paper industries have lost significant market share due to the advent of electronic media. In fact, over the last two decades, the detriment has been so severe that several large producers started taking major permanent closures and even began a practice of pre-emptive shutdowns to balance a market in permanent decline before operating rates and prices collapsed.

In this context, it has been crucially necessary to consider other options for the various products and byproducts typically produced by the paper industry and other bio-based industries. Accordingly, it would be advantageous to provide systems and methods that could economically benefit the above respective industries such as by synergistically combining, utilizing, and/or improving upon the various systems and methods in various bio-based areas, such as the cellulosic ethanol and biochemical (e.g., biofuels) industries and pulp and paper industries.

SUMMARY OF THE INVENTION

The present invention relates to systems and methods that can utilize cellulosic feedstock for producing industrial carbohydrate streams (e.g., sugar streams, fiber streams, and the like), such as for biochemical (e.g., biofuel) production.

In one embodiment, a method for producing a carbohydrate stream from a cellulosic feedstock can include mixing a cellulosic feedstock with at least one enzyme and a liquid to produce a slurry and begin enzymatic hydrolysis of the cellulosic feedstock. The slurry can be subjected to a carbohydrate conversion step to further hydrolyze the cellulosic feedstock in the slurry from oligosaccharides and/or disaccharides to C5 and/or C6 simple sugars and produce a stream including the C5 and/or C6 simple sugars, the at least one enzyme, and unhydrolyzable components. After the carbohydrate conversion step but prior to further processing of the C5 and/or C6 simple sugars, the stream can be separated into a solids portion including the unhydrolyzable components and a liquid portion including the C5 and/or C6 simple sugars and the at least one enzyme, wherein the liquid portion defines a carbohydrate stream where at least 50% of total sugar in that stream is the C5 and/or C6 simple sugars and/or where the total unhydrolyzable solids fraction of the stream is less than or equal to 30% of the total solids content. And then, the at least one enzyme can be separated from the liquid portion. In one example, the method can further include recycling the separated enzyme to a step earlier in the method for reuse.

In another embodiment, a method for producing a carbohydrate stream from a cellulosic feedstock can include mixing a cellulosic feedstock including brown stock with at least one enzyme, which includes a recycled enzyme from a step later in the method, and a liquid to produce a slurry and begin enzymatic hydrolysis of the cellulosic feedstock. The slurry can be subjected to a carbohydrate conversion step to further hydrolyze the cellulosic feedstock in the slurry from oligosaccharides and/or disaccharides to C5 and/or C6 simple sugars and produce a stream including the C5 and/or C6 simple sugars, the at least one enzyme, and unhydrolyzable components. After the carbohydrate conversion step but prior to further processing of the C5 and/or C6 simple sugars, the stream can be separated into a solids portion including the unhydrolyzable components and a liquid portion including the C5 and/or C6 simple sugars and the at least one enzyme, wherein the liquid portion defines a sugar stream where at least 50% of the total sugar in that stream is the C5 and/or C6 simple sugars and/or where the total unhydrolyzable solids fraction of the stream is less than or equal to 30% of the total solids content. The liquid portion can be separated, via ultrafiltration and/or nanofiltration, into a permeate including the C5 and/or C6 simple sugars and a retentate including the at least one enzyme, and the separated enzyme recycled to the earlier mixing step in the method for use as the recycled enzyme. And the C5 and/or C6 simple sugars can be recovered in the permeate.

In another embodiment, a system for producing a carbohydrate stream from a cellulosic feedstock can include a mixer in which cellulosic feedstock mixes with at least one enzyme and a liquid to produce a slurry and begin enzymatic hydrolysis of the cellulosic feedstock. The system can further include a carbohydrate conversion system that receives the slurry and whereat the cellulosic feedstock is further hydrolyzed from oligosaccharides and/or disaccharides to C5 and/or C6 simple sugars to produce a stream including the C5 and/or C6 simple sugars, the at least one enzyme, and unhydrolyzable components. The system can further include a first separation device that receives and separates the stream into a solids portion including the unhydrolyzable components and a liquid portion including the C5 and/or C6 simple sugars and the at least one enzyme, wherein the liquid portion defines a carbohydrate stream where at least 50% of total sugar in that stream is the C5 and/or C6 simple sugars and/or where the total unhydrolyzable solids fraction of the stream is less than or equal to 30% of the total solids content. The system can further include a second separation device that receives the liquid portion including the C5 and/or C6 simple sugars and the at least one enzyme and separates the at least one enzyme from the liquid portion, whereby the separated enzyme is recycled to the mixer for reuse.

The features and objectives of the present invention will become more readily apparent from the following Detailed Description taken in conjunction with the accompanying drawings.

DETAILED DESCRIPTION OF THE INVENTION

Figure 1:
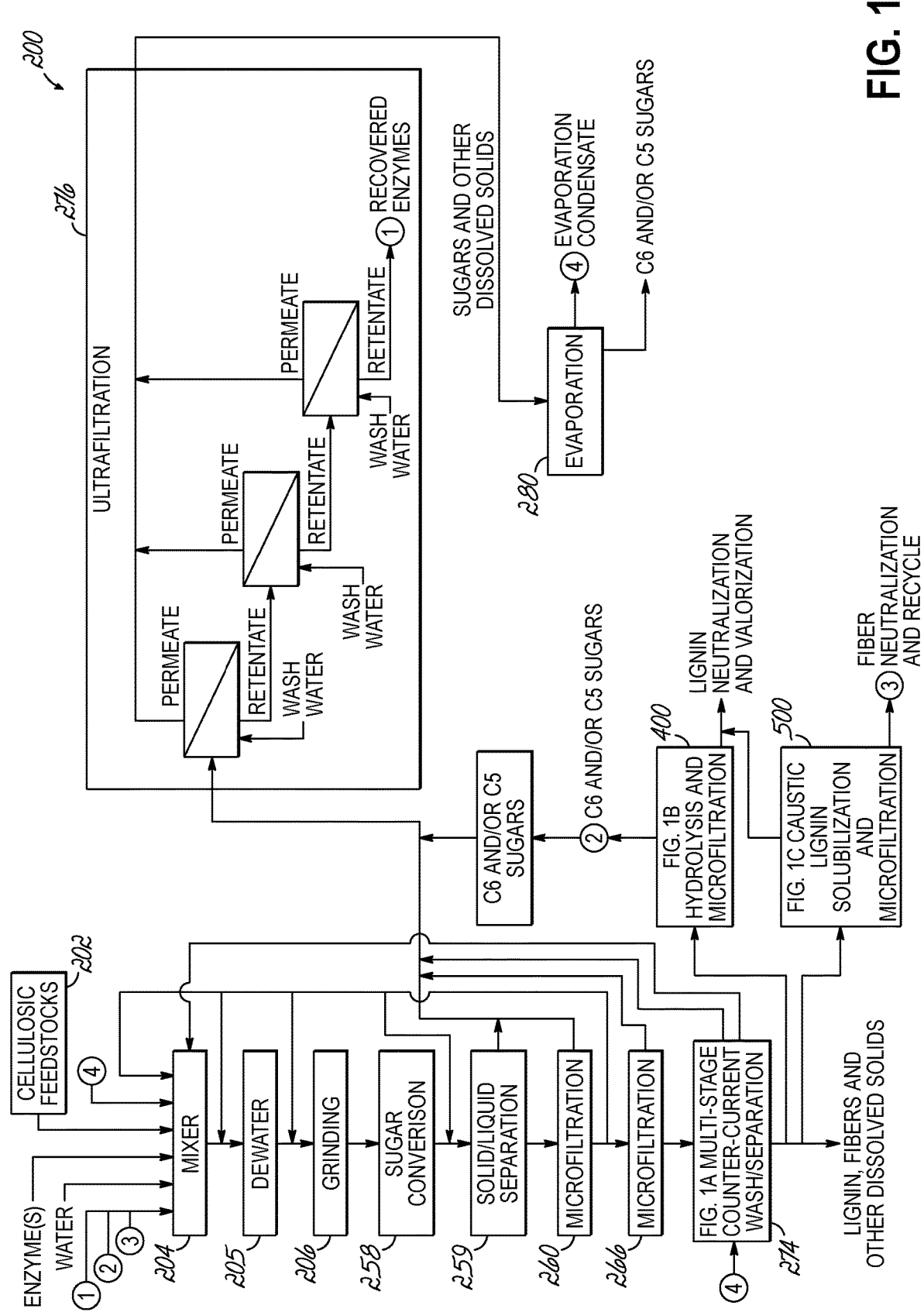
FIG. 1 depicts a flow diagram illustrating a system and method for producing a carbohydrate stream (e.g., sugar stream) from a cellulosic feedstock in accordance with an embodiment of the invention.
Figure 2:
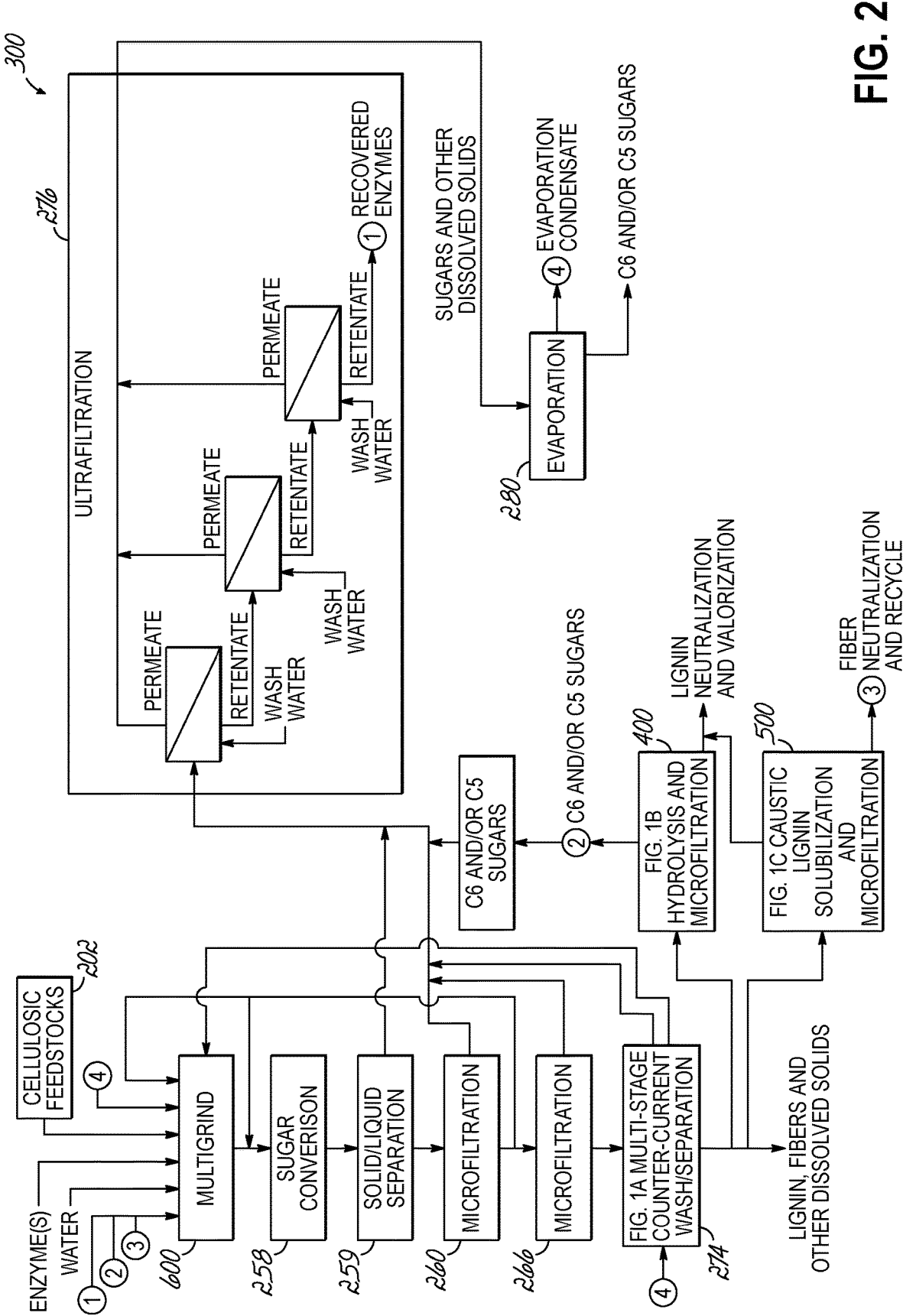
FIG. 2 depicts a flow diagram illustrating a system and method for producing a carbohydrate stream (e.g., sugar stream) from a cellulosic feedstock in accordance with another embodiment of the invention.
Figure 2A:
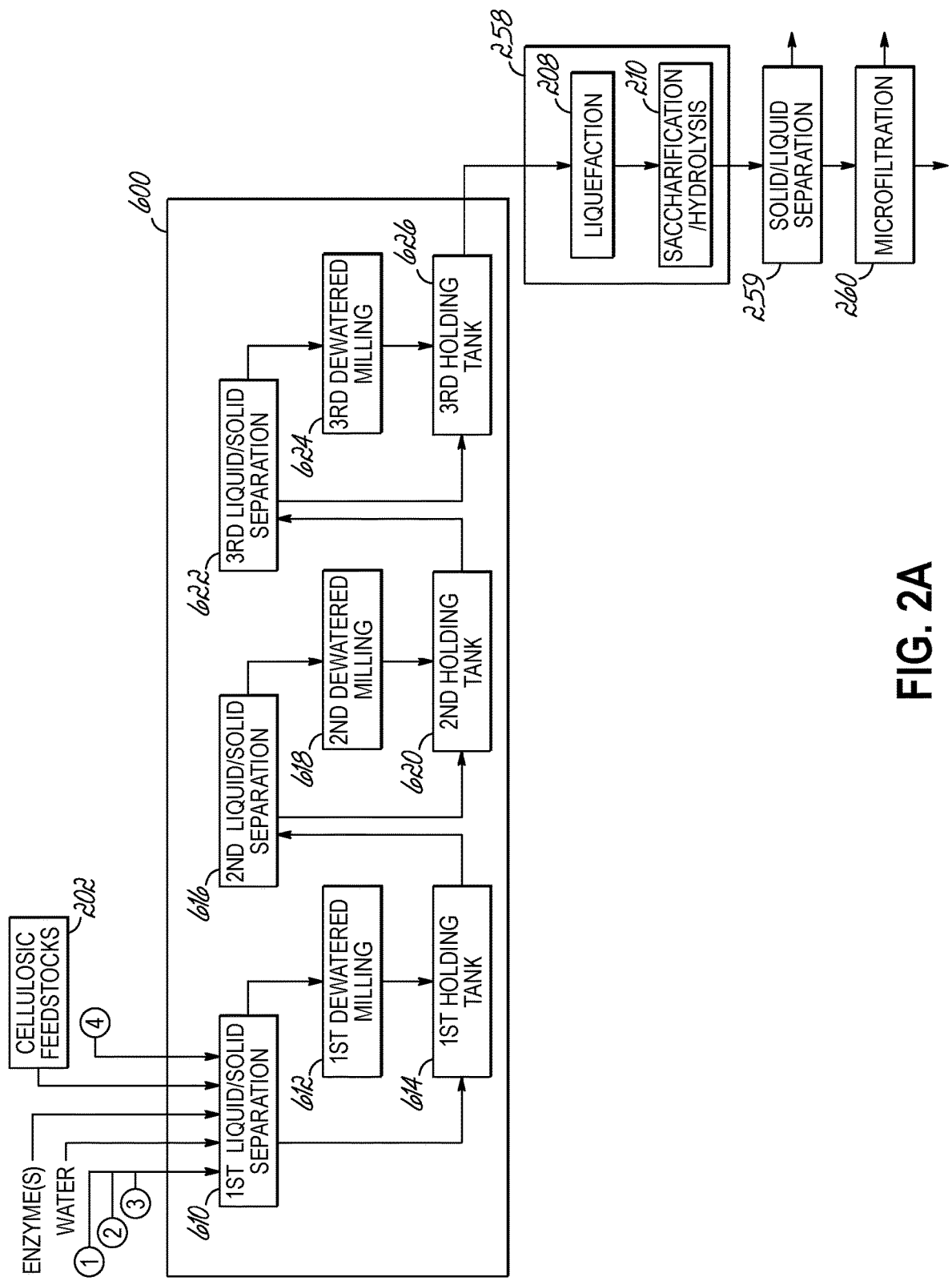
FIG. 2A depicts a flow diagram further illustrating the multi-grind step of the system and method for producing a sugar stream of FIG. 2.

FIGS. 1-2A illustrate systems and methods 200, 300 for producing carbohydrate (e.g., sugar) streams (and recycling enzymes) from a pretreated or untreated biomass such as cellulosic feedstock, including, for example, "brown stock" feedstock, or waste or recycled fiber sludge produced in the pulp and paper industry, such as for biochemical (e.g., biofuel) production, in accordance with the present invention. In one example, the system and method 200, 300 can produce high purity C6 (glucose and/or fructose) and/or C5 (xylose) sugar streams from cellulosic feedstocks, such as brown stock or waste fiber sludge, that can be effectively converted into various biochemical products, such as ethanol. As another option, grain-based feedstocks or agricultural/food waste by-products (e.g. apple and citrus peels) may be used in the systems and methods 200, 300.

As further discussed in detail below, a sugar/carbohydrate stream, which has had removed therefrom an undesirable amount of unfermentable and/or unhydrolyzable components, can be produced from a cellulosic feedstock, such as a brown stock, and/or waste fiber sludge feedstock, after liquefaction and/or saccharification and prior to any downstream sugar/carbohydrate conversion process, with such sugar/carbohydrate stream being available for biochemical production, or other processes. Grain-based feedstocks or agricultural by-products (e.g. apple and citrus peels) may be used here as well. In addition, the present system and method 200 also can involve the removal of certain solids and unfermentable and/or unhydrolyzable products, prior to downstream conversion or processing systems, as further discussed below. In other words, carbohydrate/sugar stream production and/or solid component separation occurs on the front end of the system and method 200, but alternative locations can also add value dependent upon where solid components are separated.

For purposes herein, in one example, the resulting sugar stream that may be desirable after liquefaction and/or saccharification, can be a stream where at least 90% of the total sugar in that stream is glucose and/or where the total insoluble (unfermentable/unhydrolyzable) solids fraction of the stream is less than or equal to 5% of the total solids content in the stream. In one example, no greater than 5% of the total solids in that stream includes non-fermentable components. In another example, the sugar stream may be a stream where at least 95% of the total sugar in that stream is glucose. Depending upon the desired sugar(s) or initial polysaccharide material, the sugar stream may further or alternatively include, for example, glucose, fructose, xylose, and/or others. In yet another example, at least 20%, 30%, 40%, 50%, 60%, 70%, or 80% of the total sugar in that stream can be glucose or combinations of glucose with another sugar(s) or carbohydrate. In another example, the total insoluble (unfermentable and/or unhydrolyzable) solids fraction of the stream is less than or equal to 3% of the total solids content in the stream. In another example, the insoluble (unfermentable and/or unhydrolyzable) solids fraction of the stream is less than or equal to 1%. In still another example, the total insoluble (unfermentable and/or unhydrolyzable) solids fraction of the stream is less than or equal to 10%, 15%, 20%, 25%, or 30%. In other words, the total fermentable content (fermentable solids fraction) of the stream may be no more than 30, 40, 50, 60, 70, 75, 80, 85, 90, 95, 97, or 99% of the total solids content in the stream. In another example, on a dry mass basis, the weight % fermentable material in the sugar stream that may be desired is greater than or equal to 80%. In another example, on a dry mass basis, the weight % fermentable material in a sugar stream is greater than or equal to 85%, 90%, 95%, 98%, or 99%.

With respect now to the cellulosic feedstock 202 that can be utilized in the system and method 200, 300 of FIGS. 1-2A, the cellulosic feedstock can be any pretreated and/or untreated cellulosic or biomass material, including diluted, concentrated, or pressed, that is ready for further processing in the systems and methods discussed further hereinbelow. In one example, the cellulosic feedstock is a pretreated cellulosic or biomass material. The cellulosic feedstock 202 can be derived from essentially any non-food or food biomass, including recycled non-food biomass. In one example, the cellulosic feedstock 202 may be brown stock that has been derived from woody biomass, from hardwood or softwood, for example, and processed in accordance with pulp and paper industry standards, including those processes known and understood in the industry by those skilled in the art. Other examples of suitable starting material for producing the cellulosic feedstock or brown stock can include boxboard/cartonboard (e.g., virgin or recycled grade), containerboard (e.g., liner or medium grade), graphic paper (e.g., wood-containing or wood-free grade), packaging paper (e.g., Kraft paper grade); pulp (e.g., dissolving, Kraft, Virgin, or recycled grade), tissue (e.g., commercial or retail grade), newspaper, copy paper, and the like, and any waste by-product that results from any processing of the aforementioned products and its associated operations, or any combination of the aforementioned, and the like. Cellulosic feedstock 202 generally can include feedstock that is composed of cellulose, hemicellulose, lignin, ash, or combinations thereof. In one example, cellulosic feedstock is composed of cellulose, hemicellulose, ash, and lignin. Cellulose, upon enzymatic or other methods of hydrolysis, can produce glucose and other C6 sugar oligomers while hemicellulose can produce xylose and other C5 sugar oligomers.

Although the system and method 200 described herein will generally focus on cellulosic feedstock 202 that defines brown stock feedstock, other non-food biomass feedstock is contemplated here, including waste fiber sludge such as pretreated tissue fiber sludge, secondary fiber sludge, woody biomass, agricultural biomass, and components thereof. In one example, tissue fiber sludge can include up to 20 wt % solids (dilute) or greater than 20 wt % solids (pressed). In one example, secondary fiber sludge can include up to 20 wt % solids (dilute) or greater than 20 wt % solids (pressed), and may contain recovered and/or recycled fiber. In addition, virtually any type of agricultural biomass or materials can be processed (as known and would be understood in the art) into the cellulosic feedstock 202 for use in the present invention. Examples of suitable food or non-food agricultural biomass materials can include stover (e.g., corn, barley, and the like), corn cobs, straw (e.g., wheat straw), sugarcane bagasse, sorghum, miscanthus, tobacco leaves and/or stalks, corn, wheat, barley, sorghum, rye, triticale, rice, oats, sugar cane, tapioca, cassava, pea, potato, apple and citrus peels (e.g., orange peels), and the like. Glucose, fructose, xylose, and/or other carbohydrates (e.g., pectin and the like), for example, may be derived from one or more of these agricultural materials.

In one example, as indicated above, the cellulosic feedstock is treated or pretreated in accordance with industry practices, e.g., pulp and paper or agricultural industry practices, to provide a cellulosic feedstock suitable for use in the system and method 200. As used herein, the terms "treated" or "pretreated" can convey and encompass those types of cellulosic feedstocks 202 that have in some way been processed, including paper pulp or fiber sludges from paper pulp processes, in accordance with industry practices. For example, the cellulosic feedstock can be paper pulp, e.g., brown stock, that generally has been washed and/or neutralized. In another example, the cellulosic feedstock can be waste fiber sludge that generally has been washed and/or neutralized. In one embodiment, the cellulosic feedstock 202 can include a dry matter content from 1 to 99% by weight. In another example, the dry matter content can be from about 10 to about 50% by weight. In yet another example, the dry matter content can be from about 15 to about 30% by weight, or 10 to 20% by weight, 10 to 19% by weight, or from 21 to 39% by weight. In another example, the dry matter content can be above 20% or below 20%. In another example, the dry matter content can be about 19% by weight. Further yet, in one example, the cellulosic feedstock 202, such as brown stock feedstock, can include on a dry basis about 0.1 to 99.9 wt % glucans, about 0.1 to 99.9 wt % xylans, ash at less than 30.0 wt %, lignin at less than 20.0 wt %, and combinations thereof. In another example, the cellulosic feedstock 202 can include a dry basis of about 50.0 to 90.0 wt % glucans or about 65.0 to 90.0 wt % glucans. In another example, the cellulosic feedstock 202 can include a dry basis of about 5.0 to 25.0 wt % xylans, or about 5.0 to 15.0 wt % xylans. In another example, the cellulosic feedstock 202 can include ash at less than 15.0 wt %, at 1.0 to 15.0 wt %, or ideally at less than 1.0 wt %. In still another example, the cellulosic feedstock 202 can include lignin at less than 20 wt %, 1.0 to 20 wt %, at less than 15.0 wt %, less than 10 wt %, less than 5 wt %, or ideally at less than 1.0 wt %. In another embodiment, treated or pretreated material, particularly with respect to the brown stock feedstock, can define a relatively high weight percent of glucans and/or xylans, when taken on a dry basis. In one example, the cellulosic feedstock or brown stock feedstock can include glucans in an amount of at least 50 to 90 wt % and/or xylans in an amount of at least 5 to 25 wt %. The particle sizes in the cellulosic feedstock 202 may range from less than a micron to about 20 mm, or from about a micron to about 10 mm.

One suitable process, among many, for providing or producing a cellulosic feedstock, particularly a brown stock feedstock, where an initial biomass material has been treated/pretreated in a manner such that the cellulosic feedstock is ready for use in the present invention is described in Freis et al., U.S. Pat. No. 4,810,328, the disclosure of which is hereby incorporated by reference herein in its entirety, and further discussed hereinbelow.

Here, virgin cellulosic fiber, for example, typically derived from logs of hardwood or softwood, can undergo lengthy processing before it can be suitable for use in papermaking, for example. In a typical pulping process, logs are reduced to wood chips, which are fed into a digester. "Liquor", an aqueous solution obtained from a later described wash step and containing dissolved and residual cooking chemicals, spent cooking chemical residue and cellulosic contaminants, and "white liquor", another by-product of the pulping process known in the art, are fed into the digester, primarily for dilution. Cooking chemicals are also added as required. The contents of the digester are brought to a relatively high temperature and pressure, for example about 177° C., at a pressure of about 110 pounds per square inch. The wood chips are "cooked" in the digester under these conditions to reduce the wood chips to pulp. Typically, under these conditions, the wood chips are cooked from about 1 to 5 hours. The cooking can be carried out in batch or continuous digesters.

The cooked wood chips or pulp in the aqueous medium after digestion is referred to as "brown stock". The brown stock consists generally of two phases, the pulp, and the liquor or liquid phase of the digester contents. However, typically after digesting, oversized chips, insufficiently cooked chips, or knots remain. These components are generally removed from the brown stock by knotters, which typically consist of coarse screens.

Before further processing of the pulp, it may be considered necessary to separate the pulp from the liquor. It can also be desirable to clean the pulp, removing and to the greatest extent possible, recovering spent or excess cooking chemicals, and removing and recovering pitch contaminants. After digestion, and following removal of oversized chips and the like, the brown stock is transferred to a washer for a washing step. Typically, the washing process involves a series of washers that separate the pulp from the liquor, and progressively clean the pulp by removal of cooking chemicals, cooking chemical residues, and non-cellulosic contaminants.

Several methods can be used to perform the washing step. In the past, the brown stock was filtered in a false bottom tank or diffuser into which the digester was discharged. The liquor was drained through the false bottom, and the pulp was washed by gravity displacement of the liquor with wash water. Other types of washers, such as a pressure washer, are also known in the art. Currently, the rotary vacuum drum or cylinder or vacuum washer is more typically used. The vacuum washer is generally a wire cylinder or drum that rotates in a vat containing the brown stock (i.e. the pulp and liquor mixture). The lower section of the drum is immersed in the brown stock. Vacuum is applied inside the drum as it rotates through the brown stock. The liquor drains through the surface of the wire drum into the interior, leaving a layer of pulp on the outside face of the drum. The layer of pulp is held in place by the vacuum force inside the drum, from where the liquor is conducted away from the pulp.

To ensure a consistency of the cleanliness of the pulp when run through the drum filter, it may be desired to "re-pulp" the pulp recovered from the drum by again diluting the pulp in a bath and scrubbing the same. Thereafter, the pulp slurry may again be separated by use of the drum filter, for example.

With regard to the cooking affected in the digester, the cooking chemicals used in pulping mills are known in the art. In general, the cooking system is either kraft or sulfite. Other cooking systems are also known in the art, and may also be used. The kraft system generally involves the use of sodium hydroxide and sodium sulfide in the digester to aid in decomposition of the wood fibers to produce pulp. The sodium may be added as sodium sulfate, sodium carbonate, or similar sodium compounds. The sulfite system typically involves the use of sulfite, and magnesium, calcium, sodium, or ammonia. The kraft mill generates "black liquor", while the counterpart in the sulfite mills is referred to as "red liquor". For purposes herein, the term "liquor" refers to both "red" and "black" liquor, and the aqueous phase of the pulp mixture resulting from other pulp processing methods such as those described below.

Some pulping mills form pulp from wood products without the use of cooking chemicals. Several such pulping processes are known, including mechanical processes such as the groundwood process, use of a refiner to create refiner mechanical pulp, or use of heat to create thermomechanical pulp. Most such processes rely on heat and mechanical action to break down the wood fibers. Other processes, such as the neutral sulfite semi chemical (NSSC) process, rely on both chemical and mechanical action. While these mechanical, thermomechanical, or semi-chemical processes typically do not involve washing steps, when washing steps are used, it can aid in cleaning the pulp and recovering organic contaminants.

Before washing, the brown stock will often contain many impurities from the pulping process, including excess cooking chemicals and spent cooking chemicals (where chemicals are used in the pulping), and also a variety of organic contaminants such as resin acids, fatty acid soaps and the like originating in wood. The contaminants occlude to the pulp fibers, and are also present in the aqueous phase of the brown stock. It has been found that in general, the contaminants of black liquor and the corresponding pulp are principally alkali lignin, hydroxy acids and lactones, and sodium. Generally, black liquor is also contaminated with acetic acid, formic acid, sulfur, extractives, and methanol. Red liquor (obtained through the sulfite process) and the corresponding pulp has been found to be laden with ligno-sulfonate, monosaccharides (mannose, xylose, galactose, glucose and arabinose), poly and oligosaccharides, calcium, aldonic acids, sugar-sulfonates, extractives, acetic acid, methanol, and glucuronic acid. These materials are substantially different from those encountered in de-inking or de-waxing re-pulping processes, where the contaminants/slurry constituents are generally inorganic substances and very different organic compounds.

As another example of providing or producing a cellulosic feedstock, fiber sludge, such as waste fiber sludge from a pulp and paper process, which may be treated/pretreated or not treated at all, can be used as the cellulosic feedstock here. In one example, fiber sludge, including residual fiber from a tissue mill sludge, that is either unwashed or may have been washed and/or neutralized may be provided as the cellulosic feedstock and processed according to the system and method 200, 300 of FIGS. 1-2A. In one example, the fiber sludge feedstock can have relatively high carbohydrate content and can be amenable to bioconversion without exotic pretreatment. In one embodiment, the fiber sludge feedstock may include 35 wt. percent water and about 65 wt. percent solids. And with regard to the solids, glucan may be present in an amount of about 65.3 wt. percent; xylan at about 13.5 wt. percent; galactan at about 0.9 wt. percent; arabinan at about 0.5 wt. percent; mannan at about 2.2 wt. percent; acid insoluble ash at about 4.4 wt. percent; acid soluble ash at about 1.3 wt. percent; volatile organic material at about 11.9 wt. percent; and lignin at about 0.68 wt. percent, with the percent calculated on a dry basis. Glucan and xylan may be converted to glucose and xylose, galactan may be converted to galactose with other sugar monomer conversions being understood here.

Figure 1A:
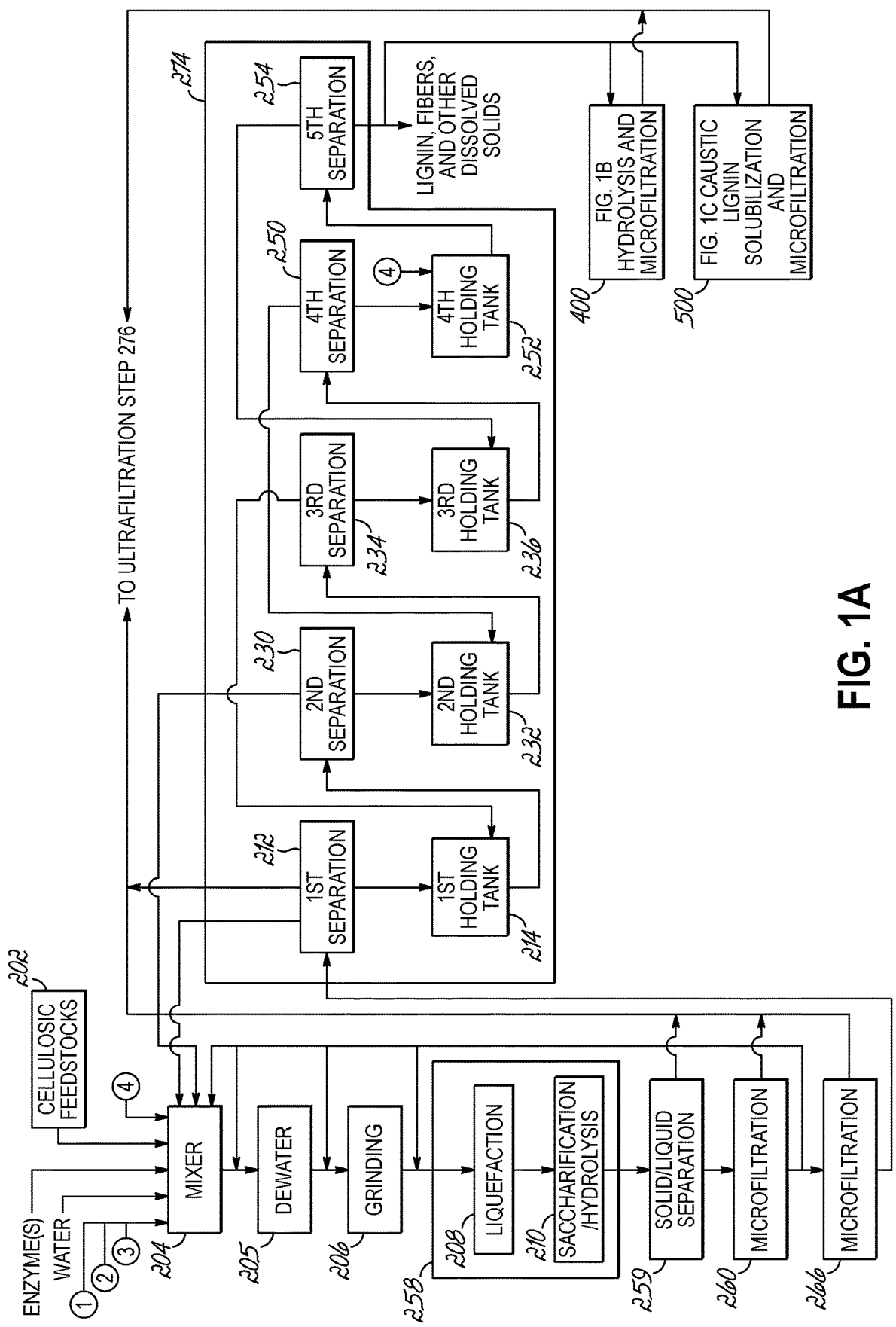
FIG. 1A depicts a flow diagram further illustrating the enzymatic hydrolysis step and the multistage countercurrent wash/separation step of the system and method for producing a sugar stream of FIG. 1.

With specific reference now to FIGS. 1 and 1A, in one embodiment of the system and method 200, cellulosic feedstock 202, e.g., brown stock (pulp) feedstock, which has been pretreated (e.g., unwashed, washed, and/or neutralized), or waste fiber sludge, can be sent to an optional mixer 204 and combined with backset liquid to help create a slurry and attain the desired total solids in the mixer 204. In an alternate embodiment, the cellulosic feedstock 202 is untreated/not pretreated. The backset liquid, identified herein as stream "4", can include evaporation condensate from an optional evaporation step 280, which is an optional later step in the method 200 and is discussed further below. Optionally, fresh water or other process waters may be added here, such as to limit the amount of backset needed, and to help attain the desired total solids. The mixer 204 may include any suitable mixer. In one example, the mixer has a rotary axis that utilizes a gravity based or free fall principle. In another example, the mixer can be a stirred tank reactor, a recirc pump, a drum mixer, a paddle mixer, a tumble mixer, or the like for enzymatic hydrolysis. Other suitable mixers can be those equipped with impellers, such as Rushton turbine, Intemig impeller, or a Scott mixer, which may be mounted on a centrally placed impeller shaft, for example. In one example, the mixer 204 may define a continuous, high shear mixer so that any larger aggregate is reduced to a relatively small particulate to produce a generally homogeneous slurry mixture. The particle sizes in the cellulosic feedstock 202 may range from about 0.05 microns to about 20 mm, or from about one micron to about 10 mm.

With continued reference to FIG. 1, in addition to backset liquid, at least one or more enzymes may be added to the cellulosic feedstock, such as at the mixer 204, to begin the process of enzymatic hydrolysis of the cellulosic feedstock, particularly polysaccharide conversion to oligosaccharides and disaccharides, and ultimately the conversion of those constituents into various C5 and/or C6 simple sugars, such as glucose, fructose, and/or xylose, for example, which can occur at the carbohydrate (e.g., sugar) conversion step 258, which is further discussed below. The one or more enzymes can be selected from endoglucanase, cellulase, B-glucanase, xylonase, hemicellulase, and the like, for example, and can be iteratively and effectively added to the formed slurry based on the amount of solids concentration or loading and, in one example, can be based on the amount of the glucan concentration or loading by weight percent as described herein below. In one example, the enzyme addition rate can be from about 100 kg enzyme solution per 1000 kg of bone-dry biomass (referred to as 1× loading). In one example, the enzyme addition rate can be varied from 1× to 10× loading or greater, dependent upon the substrate. In another example, the enzyme addition rate can be based upon glucan loading in the feedstock 202. Examples of suitable enzyme mixtures for use in the present invention for cellulosic hydrolysis are available from Metgen of Kaarina, Finland under the tradename Metzyme®. Other suitable enzyme additives also may be available from Novozymes, DuPont, and other commercial providers. A pH buffer, such as sulfuric acid or the like, also can be added to the cellulosic feedstock, such as at the mixer 204, to lower or raise the pH of the slurry, as needed, such as within a pH range of about 4.0 to 6.5, for example. In one example, the pH is about 5.0. Other pH ranges of the slurry may be suitable to match the optimal enzyme activity.

When the cellulosic feedstock forms the slurry at the mixer 204, in one example, it may include a concentration of about 1.0 to 50.0 wt % solids. In another example, the concentration may include 10.0 to 40.0 wt % solids, in another example, 10.0 to 20.0 wt % solids, and in another example 5.0 to 10% wt % solids. The slurry further may be maintained at a temperature from about 30° C. to 70° C., and more preferably at about 40-60° C. In another example, the slurry can be maintained at a temperature from about 27° C. to about 66° C. or, in another example, at about 50° C. The temperature of the slurry can be dependent upon the optimal temperature of the enzyme(s) used for the conversion process. Thus, temperature ranges outside those listed above may be suitable. The residence time within the mixer 204 can range from about 1 to 80 hours. In another example, the residence time in the mixer can range from about 16 to 30 hours or, in another example, from about 8 to 12 hours or about 10 hours. Alternatively, the residence time within the mixer 204 can range from about 1 to 60 minutes.

The enzyme(s) utilized here are understood to shorten the required residence time so as to optimize the hydrolysis reaction. With this system and method 200, it is believed that the life-expectancy or operational efficacy of these enzymes are at least about two times that of other single-pass processes and perhaps potentially as high as ten times or more of other single-pass processes, thereby realizing substantial savings in capital, operational, and system expenses. It also has been found that viscosity decreases with an increase in residence time, and that density increases with an increase in residence time. The viscosity and ability to maintain solids in suspension (via agitation) can help determine the ideal TSS (total suspended solids) level, which can be about 5 wt % of the slurry, in one example, and can range up to about 10 wt % or up to about 20 wt % of the slurry. In another example, the TSS can range from about 1 to 5 wt % of the slurry. Stated another way, it is understood that cellulosic material hydrolysis occurs as a function of time and enzyme concentration, as further discussed below. Oligomers and/or dimers of glucans and xylans, in solution, can hydrolyze to form glucose and xylose, respectively, as also further discussed hereinbelow.

Other inputs to the mixer 204 can include recovered/recycled enzymes (along with sugars, and other dissolved solids) identified herein as stream "1"; C6 and/or C5 sugars (along with other dissolved substances) identified herein as stream "2"; neutralized fiber identified herein as stream "3"; and others. The addition of the recovered enzymes at stream 1 here presents a cost savings and is understood to help result in substantially accelerated hydrolysis as compared to known processes, which is further discussed below. The additional sugars from stream 2 can be provided at a relatively lower pH. Accordingly, if the cellulosic feedstock 202 needs to be buffered to reduce the pH, stream 2, which can be provided from an optional hydrolysis/microfiltration step 400, as explained below, can provide the necessary acidity. Stream 3, which includes neutralized fiber, may be provided to the mixer 204 from an optional caustic lignin solubilization/microfiltration step 500 as further explained below. Stream 3 contains neutralized recalcitrant fiber and other dissolved solids that may be recirculated to the mixer 204 for continued (re)processing in the system and method 200.

The slurry stream from the mixer 204 next may be subjected to an optional dewater step 205 to remove liquid from the slurry stream. The dewater step 205 uses dewatering equipment, e.g., a paddle screen, a vibration screen, screen decanter centrifuge or conic screen centrifuge, a pressure screen, a preconcentrator, and the like, to accomplish removal of liquid from the slurry stream. The removed liquid portion can be sent on to sugar conversion step 258, returned to dewater step 205, and/or returned to mixer 204.

The dewatered slurry stream from the dewater step 205, the slurry stream from the mixer 204 if the optional dewater step 205 is not present, or the slurry stream formed without mixer 204 (if not present), next may be subjected to an optional grinding/particle size reduction step 206, which may involve use of a disc mill, roller mill, hammer mill, flaking mill, homogenizer, or the like, to grind the cellulosic feedstock slurry to average particle sizes of less than about 2000 micron and facilitate the additional release of cellulose complexes therefrom. In another example, the particle sizes range from about 1000 micron to 850 micron. In another example, the particle sizes range from about 1000 micron to 500 mm. In another example, the particle sizes range from about 800 micron to 250 micron. The grinding further helps continue to break up the bonds between fiber and polysaccharides as well as further exposes cellulosic surfaces to enzymatic breakdown.

The further ground feedstock slurry, or the stream from the mixer 204 or the slurry stream formed without the mixer 204, if the grinding step 206 is not provided, next may be subjected to sugar conversion step 258, which can include, as shown in FIG. 1A, a liquefaction step 208 and/or a saccharification or hydrolysis step 210. Further with respect to the liquefaction step 208, various liquefaction processes can be utilized to help further hydrolyze the cellulosic feedstock in the slurry to oligosaccharides, disaccharides, and eventually into its simple sugar(s). In one example, hydrolysis begins with the slurry material being further mixed in a tank (or the like) with enzyme(s), as described above, including endoglucanase, cellulase, B-glucanase, xylonase, hemicellulase, and the like, or combinations thereof. The pH can be further adjusted here to about 5.0 and the temperature may be maintained between about 40° C. to 60° C. (e.g., 50° C.) so as to allow for the enzyme activity to further hydrolyze the cellulosic feedstock slurry to smaller components, such as disaccharides and eventually into a simple sugar(s). Other pH ranges, such as from pH 4.0-8.0 or 4.0-7.0, may be utilized and an acid treatment system using sulfuric acid, for example, can be used as well for pH control and further conversion of the slurry to sugars. In addition, other temperature ranges of greater than 60° C. or less than 40° C. can be utilized for further conversion of the slurry to sugars.

The stream from the liquefaction step 208 can contain particle sizes that range from about 50 micron to about 3 mm. This stream next can be further subjected to an optional saccharification or hydrolysis step 210 whereat oligosaccharides and disaccharides, for example, can be further hydrolyzed in a tank or the like to simple sugars, such as single glucose sugar molecules, as well as potentially xylose, fructose, and the like, for example. Other disaccharides and oligosaccharides of various length and molecular weight also can be produced here, for example. In particular, at the saccharification or hydrolysis step 210, the slurry stream may be at or adjusted to a pH of about 3.5 to 7.0, with the temperature being maintained between about 30° C. to 70° C. for 1 to 6 hours to further help convert the oligosaccharides and disaccharides in the slurry to simple sugars, such as glucose. In another example, the pH can be 5.2 to 5.8 or 5.5, for example. In another example, the temperature can be maintained at 40-60° C. for about 5 hours. In another example, the reaction time can be between 5 hours and 75 hours. Also, an enzyme(s), such as one or more enzymes selected from endoglucanase, cellulase, B-glucanase, xylonase, hemicellulase, protease, and the like, or combinations thereof, may be added here. Other enzymes or similar catalytic conversion agents may be added at this step or previous steps that can enhance the polysaccharide conversion to sugar or yield other benefits.

A liquefied or hydrolyzed sugar stream having a density of about 1.00 to 1.15 grams/cc can result here. At this point, the sugar stream, whether or not optionally subjected to the saccharification or hydrolysis step 210, can be a stream where at least 90% of the total sugar in that stream can be glucose and/or where the total insoluble (unfermentable and/or unhydrolyzable) solids fraction of the stream can be less than or equal to 5% of the total solids content in the stream. In another example, the total insoluble (unfermentable and/or unhydrolyzable) solids fraction of the stream can be less than or equal to 30% of the total solids content in the stream. Depending upon the desired sugar(s) or initial polysaccharide material, the sugar stream may include, for example, glucose, fructose and/or xylose, or others. In yet another example, at least 20%, 30%, 40%, 50%, 60%, 70%, or 80% of the total sugar in that stream can be glucose or combinations of glucose with another sugar(s). In this example, the sugar stream may not be considered desirable or "clean" enough, such as for use in biochemical (e.g., biofuel) production, because the total fermentable content of the stream may be no more than 75% of the total solids content in the stream. In this example, the liquefied sugar stream can have a total solids fraction that may range from about 5-30%, 7-12%, or 10-20%, such solids including fiber, and other materials, for example. In yet another example, the total fermentable content of the stream is no more than 30, 40, 50, 60, or 70% of the total solids content in the stream.

Although shown as separate steps in FIG. 1A, the liquefaction and saccharification or hydrolysis steps 208, 210 may be combined into a multistage continuous (or batch) process, such as via a vertical or horizontal continuous reactor. In one example, the high shear mixer 204 can fluidly communicate with a vertical or horizontal continuous multistage enzymatic hydrolysis reactor at sugar conversion step 258. The vertical or horizontal vessel(s) can be designed to be internally baffled to create multizone mixing, which can simulate multiple continuous stirred-tank reactors in series. As indicated above, the residence time within the reactor at the sugar conversion step 258 can range from 2 to 80 hours and, in one example, can be from 8 to 12 hours when enzyme loading is optimized and increased. As used throughout this application, the term "multistage" can include a range of 1 to 100 stages.

As discussed above, along with the fresh enzymes, several other streams, identified by numerals 1, 2, and 3, may be added to the mixer 204 in much the same way that the backset (evaporation condensate), as stream 4, is added from the evaporation step 280. Concerning stream 1, this stream again contains recovered enzymes (and sugars, and other dissolved solids) from an ultrafiltration step 276 later in the process, which is further discussed below. The addition of the recovered enzymes presents a cost savings given the reuse and recycle of enzymes in the present process. Yet further, the present process is understood to result in substantially accelerated hydrolysis due to a cost-efficient increase in the enzyme activity or concentration, as compared to known processes, within the reactor at the sugar conversion step 258. For example, the residence time can be reduced from 50 to 80 hours to about 10 hours (or less). In sum, the present invention can reduce the effective residence time within the reactor due to increased enzyme concentration, and, as a function of unit volume dissolved solids produced.

After the sugar conversion step 258, the hydrolyzed and/or saccharified stream, which now defines a sugar stream, can be subjected to an optional solid/liquid separation step 259, such as after the suspended solids level reaches about 5 wt % slurry. Viscosity and the ability to maintain solids in suspension (via agitation, homogenization, and the like) will determine ideal total suspended solids (TSS) levels. More specifically, the resulting sugar stream from the enzymatic hydrolysis step 258 can be subjected to the solid/liquid separation step 259, which can include one or more separation devices, in series and/or parallel, to define a multistage solid/liquid separation step 259, so as to separate the sugar stream into a liquid portion, including sugars (C6 and/or C5 sugars), enzymes, and other dissolved solids (e.g., ash), that defines a permeate, and a solids portions that defines a concentrate or retentate, which includes solids (soluble and insoluble), such as fibers (e.g., lignin, unhydrolyzed cellulose, etc.).

In one example, the solid/liquid separation step 259 separates the sugar stream using dewatering and/or separation equipment, e.g., a paddle screen, a vibration screen, screen decanter centrifuge or conic screen centrifuge, a disc nozzle centrifuge, a pressure screen, a pre-concentrator, a filter press, clarifier, dorclone, microfiltration unit(s), or the like, to accomplish substantial separation of the solids portion and the liquid portion. This separation step 259 can utilize screen devices based on particle size and/or density, and/or other known separation systems based on G-Force, screens, surface area, or a combination thereof. Concerning the solid/liquid separation step 259 and its resulting permeate and concentrate streams, composition and concentration are substrate dependent and depend, in part, on viscosity, fiber loading, pressure drop, total membrane pressure (TMP), and permeate flow, as well as membrane capital expenditures, system power consumption, and permeate flow as a function of membrane surface area, for example. The permeate can be sent on to ultrafiltration step 276, which is further discussed below. A portion of the resulting concentrate from the solid/liquid separation step 259 may be recirculated back to the mixer 204, dewater step 205, grinding step 206, sugar conversion step 258, exit as a discharge stream from the solid/liquid separation step 259, or combinations thereof. The amount of the concentrate recirculated can be from 1-99% of the dry solids contained within the concentrate stream. In one example, the amount recirculated to the mixer 204 is one that maintains a desirable mass balance. The concentrate or remaining portion of the concentrate from the solid/liquid separation step 259, or the hydrolyzed and/or saccharified stream from the sugar conversion step 258 if the solid/liquid separation step 259 is not present, may be sent to a first microfiltration step 266.

If the solid/liquid separation step 259 is not present, the hydrolyzed and/or saccharified stream, which now defines the sugar stream, can be subjected to the first microfiltration step 260, such as after the suspended solids level reaches about 5 wt % slurry. Here again, viscosity and the ability to maintain solids in suspension (via agitation, homogenization, and the like) will determine ideal total suspended solids (TSS) levels. More specifically, the resulting sugar stream from the enzymatic hydrolysis step 258 or the concentrate (or remaining portion of the concentrate) from the solid/liquid separation step 259 can be subjected to the first microfiltration step 260, which can include one or more microfiltration units, in series and/or parallel, to define a multistage microfiltration step 260, so as to filter or separate out sugars (C6 and/or C5 sugars), enzymes, and other dissolved solids (e.g., ash), as the permeate, from the concentrate or retentate, which includes solids (soluble and insoluble), such as fibers (e.g., lignin, unhydrolyzed cellulose, etc.).

In one example, the first microfiltration step 260 includes a single microfiltration unit, but may include two, three, or more, e.g., up to 100 units. In addition, for a multistage setup, the screen or porosity opening sizes for the microfiltration units may decrease in size. With a multistage setup, the resulting concentrate from the first microfiltration unit would be further subjected to a microfiltration unit and so on. In one example, a cross-flow microfilter, or any other effective filtration means such as a dead-end filter, can be used and is sized/rated to remove micron-sized or larger particles from the sugar stream. Suitable cross-flow type microfilters include Scepter® membranes available from Graver Technologies of Glasgow, Del., which can be rated at 0.1 micron porosity, for example. The filters may be polymeric, steel, or ceramic, and can be tubular or spiral wound, for example. In one example, the filter porosity or rating here may be from about 0.05 to 3.0 microns, or from 0.1 to about 1.0 microns. The microfiltration step 260 can include a holding or feed tank that is in fluid communication with a cross-flow microfiltration unit for filtering the sugar stream received from the enzymatic hydrolysis step 258. In other examples, microfiltration units may be replaced by membrane filtration, precoat/diatomaceous earth filter, drum filter, centrifuge, or the like, which may also produce a mixed and/or single sugar stream.

Concerning the first microfiltration step 260 and its resulting permeate and concentrate streams, composition and concentration are substrate dependent and depend, in part, on viscosity, fiber loading, pressure drop, total membrane pressure (TMP), and permeate flow, as well as membrane capital expenditures, system power consumption, and permeate flow as a function of membrane surface area, for example. The permeate can be sent on to ultrafiltration step 276, which is further discussed below. A portion of the resulting concentrate from the microfiltration step 260 may be recirculated back to the mixer 204, dewater step 205, grinding step 206, sugar conversion step 258, exit as a discharge stream from the microfiltration step 260, or combinations thereof. The amount of the concentrate recirculated can be from 1-99% of the dry solids contained within the concentrate stream. In one example, the amount recirculated to the mixer 204 is one that maintains a desirable mass balance. The concentrate or the remaining portion of the concentrate from the first microfiltration step 260 may be sent to an optional second microfiltration step 266.

Like the first microfiltration step 260, the optional second microfiltration step 266 can include one or more microfiltration units, in sequence (series and/or parallel), to define a multistage microfiltration step 266, so as to filter or separate out additional sugars (C6 and/or C5 sugars), enzymes, and other dissolved solids (e.g., ash), as the permeate, from the concentrate or retentate, which includes solids, such as fibers (e.g., lignin, unhydrolyzed cellulose, etc.). In one example, the second microfiltration step 266 includes a single microfiltration unit, but may include two, three, or more, e.g., up to 100 units. In addition, for a multistage setup, the surface area of the microfiltration units may decrease. With a multistage setup, the resulting concentrate from the first microfiltration unit would be further subjected to a microfiltration unit and so on. In one example, a cross-flow microfilter, or any other effective filtration means such as a dead-end filter, can be used and is sized/rated to remove micron-sized or larger particles from the sugar stream. The filters may be polymeric, steel, or ceramic, and can be tubular or spiral wound, for example. Suitable cross-flow type microfilters include Scepter® membranes available from Graver Technologies of Glasgow, Del., which can be rated at 0.1 micron porosity, for example. In other examples, cross-flow microfilters may be rated at a larger porosity greater than or equal to 0.1 micron. In one example, the filter porosity size here may be from about 0.05 to 3.0 microns, or from about 0.1 to 1.0 microns. The second microfiltration step 266 can include a holding or feed tank that is in fluid communication with a cross-flow microfiltration unit for filtering the concentrate stream received from the first microfiltration step 260. In other examples, microfiltration may be replaced by membrane filtration, precoat/diatomaceous earth filter, drum filter, centrifuge, or the like, which may produce a more desirable sugar stream.

For the resulting permeate and concentrate streams, composition and concentration are substrate dependent and depend, in part, on viscosity, fiber loading, pressure drop, total membrane pressure (TMP), and permeate flow, as well as membrane capital expenditures, system power consumption, and permeate flow as a function of membrane surface area, for example. The permeate can be joined up with the permeate from the first microfiltration step 260 and sent on to ultrafiltration step 276, which is further discussed below. And the resulting concentrate, which includes cellulosic fiber and lignin, from the second microfiltration step 266 may be sent to optional multistage countercurrent wash/separation step 274 for further processing.

With further reference to FIG. 1A, at the optional multistage countercurrent wash/separation step 274, the concentrate from the second microfiltration step 266, or the first microfiltration step 260 if the second microfiltration step 266 is not present, can be subjected to a first separation step 212. The first separation step 212 separates the concentrate, which can include residual sugars, fine solids, cellulosic fiber, and lignin, using dewatering and/or separation equipment, e.g., a paddle screen, a vibration screen, screen decanter centrifuge or conic screen centrifuge, a disc nozzle centrifuge, a pressure screen, a pre-concentrator, a filter press, clarifier, dorclone, microfiltration unit(s), or the like, to accomplish substantial separation of the solids portion, primarily fiber (e.g., cellulosic fiber and lignin), from the liquid portion, which includes residual sugar (e.g., glucose), enzymes, and other dissolved solids. This separation step can utilize screen devices based on particle size and/or density, and/or other known separation systems based on G-Force, screens, surface area, or a combination thereof. The solids portion, which may have a total solids fraction of about 39%, may be sent on to a first holding tank 214 and the liquid portion or sugar stream from the first separation step 212 may be sent on to ultrafiltration step 276. Further yet, the sugar stream from the first separation step 212 also may be sent directly to an outside fermentation step (not shown), to convert the sugar to alcohol, such as ethanol or butanol, or any other fermentation conversion process or similar carbohydrate/sugar utilization process, as desired.

In one example, the dewatering equipment at the first separation step 212 is a paddle screen, which includes a stationary cylinder screen with high speed paddles with rakes. The number of paddles on the paddle screen can be in the range of 1 paddle per 4 to 8 inches or more of screen diameter. The number of paddles on the paddle screen can be modified depending on the amount of solids in the feed. The gap between the paddle screen and paddle can range from about 0.04 to 0.2 inch. A smaller gap gives a drier cake with higher capacity and purer fiber, but loses more fine fiber to the filtrate stream. A larger gap gives a wetter cake with lower capacity and purer liquid (less insoluble solid). The paddle speed can range from about 100 to 1,200 RPM. In another example, the paddle speed can range from 800 to 900 RPM. A higher speed provides higher capacity, but consumes more power. One suitable type of paddle screen is the FQ-PS32 paddle screen, which is available from Fluid-Quip, Inc. of Springfield, Ohio.

The screen for the dewatering equipment can include a wedge wire type with slot opening or a round hole, thin plate screen. The round hole screen can help prevent long fine fiber from going through the screen better than the wedge wire slot opening, but the round hole capacity is lower, so more equipment may be required if using round hole screens. The size of the screen openings can range from about 25 micron to 600 micron. In another example, the screen opening can range from 250 to 450 micron. In another example, the size of the screen openings can range from about 25 micron to 300 micron. In another example, the screen openings can range from 40 to 85 micron. In yet another example, the screen openings are about 45 microns. It is contemplated that larger or smaller screen sizes may be utilized here.

Returning now to the first holding tank 214, the dewatered solids portion of the stream (about 70 to 25% water) next can be subjected to a second separation step 230. And as with the first separation step 212, the second separation step 230 uses dewatering or filtration equipment, e.g., a paddle screen, a vibration screen, a filtration, scroll screen or conic screen centrifuge, a disc nozzle centrifuge, a pressure screen, a pre-concentrator and the like, to accomplish further separation of the solids portion, primarily fiber, from the liquid portion, which primarily includes sugar, enzymes, and other dissolved solids. In one example, the dewatering equipment is a paddle screen, as above described. In one example, the screen size used in the second separation step 230 can range from 25 micron to 650 micron. In another example, the screen opening can range from 250 to 450 micron. In another example, the screen openings can range from 40 to 85 micron. In yet another example, the screen openings are about 45 microns. With the second separation step 230, the actual screen openings may be larger in size than those in the first separation step 212. Screen size is dependent upon the desired separation efficiency and the overall sugar recovery yield. Water or other liquid process streams, with and without sugar or other solids, can be added to the solid portion (separated cake stream) from first holding tank 214 prior to further processing at second separation step 230.

The resulting solids portion from the second separation step 230 is sent on to a second holding tank 232 and the liquid portion or filtrate, may be joined up with the cellulosic feedstock at mixer 204 as part of a counter current washing setup. The resulting solids portion may have a total solids fraction of about 35%, with the filtrate having a total solids fraction of about 26%. Solids may range from 2% to more than 40%. The filtrate can contain particles (e.g., fine fiber) having sizes smaller than the screen size openings used in the second separation step 230.

From the second holding tank 232, the wet cake or dewatered solids portion of the stream can be subjected to a third separation step 234. The third separation step 234 uses dewatering equipment, e.g., a paddle screen, a vibration screen, a filtration, scroll screen or conic screen centrifuge, disc nozzle centrifuge, a pressure screen, a pre-concentrator, a press and the like, to accomplish further separation of the solids portion, primarily fiber, from the liquid portion, which primarily includes sugar, enzymes, and dissolved solids. In one example, the dewatering equipment is a paddle screen, as above described. With the third separation step 234, the actual screen openings may be larger in size than those in the second separation step 230. In one example, the screen size used in the third separation step 234 can range from 100 micron to 500 micron. In another example, the screen openings can range from 150 to 300 micron. In yet another example, the screen openings are about 200 microns. It is contemplated that the actual screen openings may be smaller or larger in size than those in the second separation step 230. Water or other liquid process streams, with and without sugar or other solids, can be added to the solid portion (separated cake stream) from second holding tank 232 prior to further processing at third separation step 234.

The resulting solids portion from the third separation step 234 is sent on to a third holding tank 236. From the third holding tank 236, the wet cake or dewatered solids portion of the stream next can be subjected to an optional fourth separation step 250. The fourth separation step 250 uses dewatering equipment, e.g., a paddle screen, a vibration screen, a filtration, scroll screen or conic screen centrifuge, a disc nozzle centrifuge, a pressure screen, a pre-concentrator and the like, to accomplish further separation of the solids portion, primarily fiber, from the liquid portion, which primarily includes sugar, enzymes, and dissolved solids. In one example, the dewatering equipment is a paddle screen, as above described. In one example, the screen size used in the fourth separation step 250 can range from 100 micron to 600 micron. In another example, the screen openings can range from 150 to 300 micron. In yet another example, the screen openings are about 200 microns. With the fourth separation step 250, the actual screen openings may be smaller or larger in size than those in the third separation step 234. Water or other liquid process streams, with and without sugar or other solids, can be added to the solid portion (separated cake stream) from third holding tank 236 prior to further processing at fourth separation step 250.

The resulting solids portion from the fourth separation step 250 is sent on to a fourth holding tank 252 and the liquid portion or filtrate, may be sent to the second holding tank 232 as part of the counter current washing operation. The resulting solids portion has a total solids fraction of 20%. The filtrate has a total solids content of 10%. Other concentrations of the solids stream and filtrate stream can be achieved by altering the operational conditions of the fourth separation step 250, for example. The solids fraction of the solids portion can range from about 5% to more than 40% here. The filtrate solids content can range from about 2% to more than 20%. The filtrate from the fourth separation step 250 contains particles having sizes smaller than the screen size openings used in the fourth separation step 302. Wash water, which can include at least a portion of the evaporation condensate from evaporation step 280, can be supplied here to the fourth holding tank 252.

From the fourth holding tank 252, the wet cake or dewatered solids portion of the stream, which has been further diluted via the addition of wash water, can be subjected to a fifth separation step 254 whereat dewatering equipment, e.g., a paddle screen, vibration screen, filtration centrifuge, disc nozzle centrifuge, pressure screen, screen bowl decanter and the like, is used to accomplish separation of the solid portion, which includes fiber (e.g., coarse fiber) from the liquid portion. The additional wash water here allows for easier separation of the stream into primarily a fiber portion, which includes cellulosic fiber and lignin, and an overflow liquid portion. Depending upon the initial feedstock, the cellulosic fiber here can include pectin and/or other carbohydrates, for example. One exemplary filtration device for the fifth separation step 254 is shown and described in Lee, U.S. Pat. No. 8,813,973, the contents of which are incorporated herein by reference. The screen openings in this step normally will be about 500 microns to help capture fine fiber, but can range from about 250 micron to about 1500 micron and greater. Residual liquid from the fifth separation step 254 may be sent to the third holding tank 236 as part of the counter current washing process. The dewatered fiber contains less than 3% starch and/or oligosaccharides (with a range from 0.5-9%).

While five separation steps 212, 230, 234, 250, 254 and four holding tanks 214, 232, 236, 252 are shown and utilized here, it should be understood that this system and method 200 may be modified to accommodate less than or more than that shown for recovering the sugar stream (e.g., glucose, fructose, and/or xylose), enzymes, and cellulosic fiber, which may include pectin, and/or lignin, with desirable yields and/or purity. For example, the system and method 200 can eliminate up to four of the separation steps and up to three of the holding tanks. In another example, at least three of the separation steps are utilized. In another example, at least four of the separation steps are utilized. Due to the sequential separation steps 212, 230, 234, 250, 254, sugars, etc. can be systematically washed off the fiber, which includes or defines a non-soluble carbohydrate fraction, so that the fiber can be concentrated at the last separation step, e.g., the fifth separation step 254, and the other components recovered and separated out, as desired. In another example, multiple separation steps and holding tanks may be replaced by one or more filtration centrifuges, which include multiple washing stages in a single centrifuge.

Figure 1B:
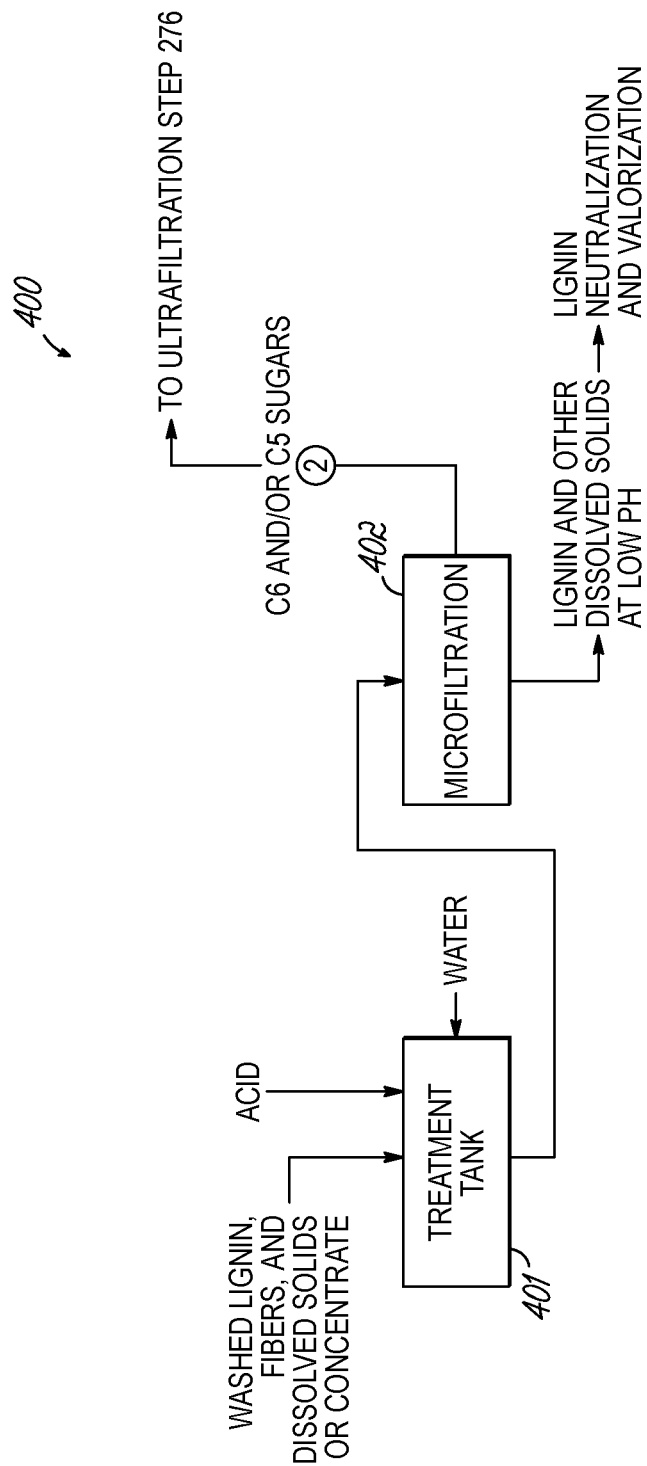
FIG. 1B depicts a flow diagram further illustrating the hydrolysis/microfiltration step of the system and method for producing a sugar stream of FIG. 1.
Figure 1C:
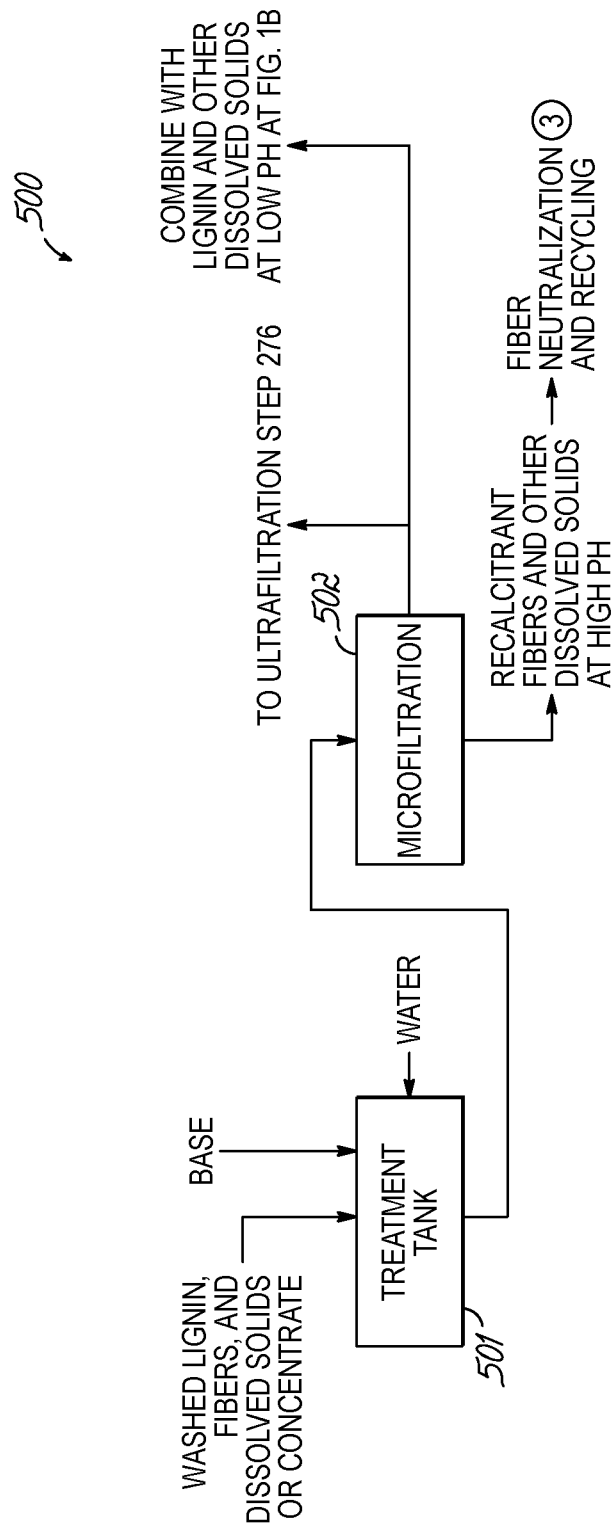
FIG. 1C depicts a flow diagram further illustrating the caustic lignin solubilization/microfiltration step of the system and method for producing a sugar stream of FIG. 1.

The washed and separated lignin (10 to 20 wt %) and cellulosic fibers (and other dissolved solids), or the concentrate from microfiltration step 260 or 266 if not subjected to the optional multistage countercurrent wash/separation step 274, now optionally may be subjected to the hydrolysis/microfiltration step 400 (FIG. 1B) and/or a caustic lignin solubilization/microfiltration step 500 (FIG. 1C). If not subjected to either optional step 400 or 500, the washed and separated lignin and cellulosic fibers (and other dissolved solids) or the concentrate may be disposed of by means and methods knows in the art, including transportation to a dumpsite, combustion, further processing to convert the lignin to high value chemicals, or the like.

Specifically concerning now FIGS. 1-1B and hydrolysis/microfiltration step 400, which includes multiple steps, the washed and separated lignin and cellulosic fibers (and other dissolved solids) or the concentrate from microfiltration step 260 or 266 initially can be subjected to a treatment tank 401, which can define a vertical or horizontal reactor, for example, whereat a suitable pH adjustment chemical, such as an acid, and water may be added thereto so as to provide a pH of about 5 or less and to create a fiber slurry. In another example, the pH can be from about 1 to about 3. The pH adjustment chemical can include sulfuric acid (e.g., 98% sulfuric acid) or the like. In one example, the process conditions for the hydrolysis of the cellulosic fibers, such as acid hydrolysis, can include the following: temperature can be from about 30° C. to 70° C., and or from about 40-60° C., or at about 50° C.; sulfuric acid concentration can include a pH from about 1 to 3, in the treatment tank 401; and residence time within the tank 401 can range from 6 to 8 hours. It will be appreciated that various process conditions may be employed here, so long as hydrolysis (e.g., acid hydrolysis) is facilitated.

With continued reference to FIG. 1B, after being subjected to acid hydrolysis at the treatment tank 401, the hydrolyzed stream next can be subjected to one or more microfiltration units 402, similar to the prior first and second microfiltration steps 260, 266. More specifically, one or more microfiltration units 402 (only one shown here), may be arranged in sequence to define multistage microfiltration that can filter or separate out residual sugars (C6 and/or C5 sugars), enzymes, and other dissolved solids as the permeate, from the concentrate or retentate, which includes solids, such as lignin, unhydrolyzed cellulose, ash, and other dissolved solids. For the resulting permeate and concentrate streams, composition and concentration are substrate dependent and depend, in part, on viscosity, fiber loading, pressure drop, total membrane pressure (TMP), and permeate flow, as well as membrane capital expenditures, system power consumption, and permeate flow as a function of membrane surface area, for example. In one example, there may include two, three, or more, e.g., up to 100 units. In one example, a cross-flow microfilter can be used and is sized to remove micron-sized or larger particles from the hydrolyzed stream. Suitable cross-flow type microfilters include Scepter® membranes available from Graver Technologies of Glasgow, Del., which can be rated at 0.1 micron porosity, for example. In other examples, cross-flow microfilters may be rated at a larger porosity greater than or equal to 0.1 micron. In one example, the filter porosity size here may be from about 0.05 to 3.0 microns, or from about 0.1 to about 1.0 microns. In other examples, microfiltration may be replaced by membrane filtration, precoat/diatomaceous earth filter, or the like, which may produce a more desirable sugar stream. Given the stream may be acidic, 304/316 stainless steel may be selected for the reactor vessel and other process equipment. Generally, the metallurgy of the microfiltration unit, including its membrane, can be determined based on the pH of the process.

The permeate, including residual sugars (C6 and/or C5 sugars), enzymes, and other dissolved solids, may be sent back the mixer 204 as stream 2, as a way to help control or adjust the pH of the feedstock slurry. Alternatively, all or a portion of the resulting permeate from the hydrolysis/microfiltration step 400 may be neutralized here and sent to ultrafiltration step 276, which is discussed below. In one example, the neutralized permeate can be combined with the permeate from the first or optional second microfiltration steps 260, 266 prior to being sent to ultrafiltration step 276. Sodium hydroxide, potassium hydroxide, and the like may be used to neutralize an acidic permeate.

The resulting concentrate, which includes solids, such as lignin, unhydrolyzed cellulose, and other dissolved solids, at low pH (e.g., about 5 or less) may be disposed of by means and methods knows in the art, including transportation to a dumpsite, combustion, further processing to convert the lignin to high value chemicals, or the like. The remaining lignin at this stage may be referred to as technical lignin, as is known and understood in the art. Alternatively, all or a portion of the resulting concentrate from the hydrolysis/microfiltration step 400 may be neutralized here, if needed, particularly the technical lignin, and utilized as a neutralized lignin feedstock, for example, for downstream valorization thereof, as is known in the art, to produce high-value chemicals. Sodium hydroxide, potassium hydroxide, and the like may be used to neutralize the acidic concentrate, if needed. The concentrate also may be subjected to other alternate treatments, including being further washed to recover residual sugars, which may be recycled back into the system and method 200, as desired.

Specifically concerning now FIGS. 1, 1A, and 1C and optional caustic lignin solubilization/microfiltration step 500, which includes multiple steps, the washed and separated lignin and cellulosic fibers (and other dissolved solids) or the concentrate from microfiltration step 260 or 266 initially can be optionally subjected to a treatment tank 501, which can define a vertical or horizontal reactor, for example, whereat a suitable base and water may be added thereto so as to provide a pH greater than 12 and to create a fiber slurry. In one example, the pH can be from about 10 to about 14. The base can include sodium hydroxide (e.g., 50% sodium hydroxide) or the like. In one example, the process conditions for the caustic lignin solubilization can include the following: temperature can be from about 30° C. to 70° C., or from about 40-60° C., or at about 50° C.; sodium hydroxide concentration can include a pH from about 10 to 13, in the treatment tank 501; and residence time within the tank 501 can range from 1 to 2 hours or be greater than 5 hours. It will be appreciated that various process conditions may be employed here, so long as caustic lignin solubilization is facilitated.

With continued reference to FIG. 1C, after being subjected to caustic solubilization at the treatment tank 501, the solubilized stream next can be subjected to one or more microfiltration units 502, similar to the prior first and second microfiltration steps 260, 266. More specifically, one or more microfiltration units 502 (only one shown here), may be arranged in sequence (series and/or parallel) to define multistage microfiltration that can filter or separate out residual sugars (C6 and/or C5 sugars), enzymes, and other dissolved solids (e.g., dissolved lignin), as the permeate, from the concentrate or retentate, which includes solids, such as lignin, unhydrolyzed cellulose, and other dissolved solids, at high pH (e.g., greater than about 12). For the resulting permeate and concentrate streams, composition and concentration are substrate dependent and depend, in part, on viscosity, fiber loading, pressure drop, total membrane pressure (TMP), and permeate flow, as well as membrane capital expenditures, system power consumption, and permeate flow as a function of membrane surface area, for example. In one example, there may include two, three, or more, e.g., up to 100 units. In one example, a cross-flow microfilter can be used and is sized to remove micron-sized or larger particles from the hydrolyzed stream. Suitable cross-flow type microfilters include Scepter® membranes available from Graver Technologies of Glasgow, Del., which can be rated at 0.1 micron porosity, for example. In other examples, cross-flow microfilters may be rated at a larger porosity greater than or equal to 0.1 micron. In one example, the filter porosity size here may be from about 0.05 to about 3.0 microns, or from about 0.1 to about 1.0 microns. In other examples, microfiltration may be replaced by membrane filtration, precoat/diatomaceous earth filter, or the like, which may produce a more desirable residual sugar stream. Given the basicity of the process, 304 stainless steel may be selected for the reactor vessel and other process equipment. Generally, the metallurgy of the microfiltration unit, including its membrane, can be determined based on the basicity of the process.

The permeate, including residual sugars (C6 and/or C5 sugars), enzymes, and other dissolved solids, such as dissolved lignin (typically at high pH), may be neutralized here and sent to ultrafiltration step 276, which is discussed below. Sulfuric acid and the like may be used to neutralize the basic permeate. Alternatively, all or a portion of the neutralized permeate from the caustic lignin solubilization/microfiltration step 500 may be utilized as a feedstock, for example, for downstream lignin valorization, as is known in the art, which can produce high-value chemicals. In one example, the neutralized permeate can be combined with the neutralized concentrate from the hydrolysis/microfiltration step 400, and then subjected to a lignin valorization process, as is known in the art, to produce high-value chemicals.

The resulting concentrate, which includes solids, such as recalcitrant or unhydrolyzed cellulose, lignin, and other dissolved solids, at high pH (e.g., greater than about 12), may be disposed of by means and methods knows in the art, including transportation to a dumpsite, combustion, further processing to convert the lignin to high value chemicals, or the like. Alternatively, all or a portion of the resulting concentrate from the caustic lignin solubilization/microfiltration step 500 may be neutralized here, particularly the recalcitrant fiber, and sent back to the mixer 204 as stream 3. Sulfuric acid and the like may be used to neutralize the basic concentrate. The concentrate also may be subjected to other alternate treatments, including being further washed to recover residual sugars, which may be recycled back into the system and method 200, as desired.

Returning now to the resulting sugar stream from the first and optional second microfiltration steps 260, 266 as well as from the optional multistage countercurrent wash/separation step 274, hydrolysis/microfiltration step 400, and caustic lignin solubilization/microfiltration step 500, at this point, the sugar stream that is ready to be subjected to further purification at ultrafiltration step 276 can be a stream where at least 30 to 90% of the total sugar on a dry solids basis in that stream is glucose. Depending upon the desired sugar(s) or initial polysaccharide material, glucose may be replaced by or the sugar stream may further include, for example, fructose and/or xylose, or others. In yet another example, at least 20%, 30%, 40%, 50%, 60%, or 70% of the total sugar in that stream can be glucose or combinations of glucose with another sugar(s). In this example, the sugar stream here may be considered desirable or "clean" enough, such as for use in biochemical (e.g., biofuel) production.

With further reference FIG. 1, the incoming sugar stream, which also includes enzymes, and dissolved solids, can be subjected to the ultrafiltration step 276, which is shown here to include three ultrafiltration units, in sequence (series and/or parallel), to define a multistage ultrafiltration step 276, to filter or separate out the enzyme(s) (and other dissolved solids and residual sugars), as the concentrate or retentate, from the sugars (C6 and/or C5 sugars) (and other dissolved solids), as the permeate. In other examples, ultrafiltration may be replaced by nanofiltration or the like, which may produce a sugar stream. In one example, one or more ultrafiltration units may be a nanofiltration unit. Yet further, a mixed C5/C6 sugar stream could be further processed by nanofiltration to separate xylose from glucose, for example. Still further, the mixed sugar stream, as in a diluted form, may be fed to a downstream bioconversion process, thereby obviating the need for an evaporation step 280 (sugar concentration step) or an ion exchange step, carbon filter step, or a diatomaceous earth filter step, for example. In other examples, ultrafiltration may be replaced by a paddle screen, vibration screen, filtration centrifuge, disc nozzle centrifuge, pressure screen, screen bowl decanter, or the like, which may produce a sugar stream.

Optional wash water (e.g., fresh or recycled) and/or other chemicals (e.g., surfactants and/or emulsifiers) may be provided at one or more of the ultrafiltration (and/or nanofiltration) units in a multistage setup to dilute the incoming residue stream so as to assist in separation of the enzymes from residual sugars and other dissolved solids. In addition, for a multistage setup, the porosity opening sizes for the filtration units may decrease in size. In one example, the ultrafiltration step 276 can include a single ultrafiltration unit, but may include two or more than three, e.g., up to 100 units, in series and/or parallel. Ultra and/or nanofilters may be spiral wound, tubular, or as otherwise designed. In one example, a polymeric membrane can be used and is sized to remove submicron-sized or smaller particles from the sugar stream. Suitable ultra and/or nanofilters can include those available from Pall Water Filtration (Cortland, N.Y.), DuPont Membrane (Wilmington, Del.), Koch Membrane (Wilmington, Mass.), and GE Water & Process Membrane, for example, which can be rated at 0.02 micron porosity, for example. In one example, the filter porosity size here may be from about 0.1 to 0.001 microns, or from 0.01 to 0.05 microns. In another example, the filter porosity size here may be from 1-10 nanometers. The ultrafiltration step 276 can include a holding or feed tank that is in fluid communication with an ultrafiltration unit for filtering the sugar stream.

Concerning the ultrafiltration step 276 and its resulting permeate and concentrate (retentate) streams, composition and concentration are substrate dependent and depend, in part, on viscosity, solids loading, pressure drop, total membrane pressure (TMP), and permeate flow, as well as membrane capital expenditures, system power consumption, and permeate flow as a function of membrane surface area, for example. The permeate, which can be combined together, can be sent on to optional evaporation step 280, which is further discussed below. The resulting retentate, which includes enzymes (and other dissolved solids and residual sugars), from the ultrafiltration step 276 may be combined together and recirculated back to the mixer 204 as stream 1. The present system and method 200 provides for the removal of most of the sugars, including C6 and/or C5, from stream 1, which is believed to contribute to enzymatic inefficiency. The amount of the concentrate recirculated can be from 1-99% of the dry solids contained within the concentrate stream. In one example, the amount recirculated to the mixer 204 is one that maintains a desirable mass balance.

After the ultrafiltration step 276, the permeate defines a more desirable sugar stream, as a result of separating out the enzymes and other insoluble components, color, ash, minerals, and the like from the sugar stream.

Concerning now optional evaporation step 280, the permeate from ultrafiltration step 276, which includes a purified or refined sugar stream of C6 and/or C5 sugars (e.g., glucose and/or xylose sugars), can be subjected to one or more evaporators or sets of evaporators, which can define a multistage evaporation step 280, where the sugars (and remaining dissolved solids) can be still further concentrated or isolated. In one example, upon being subjected to the evaporation step 280, the sugar stream can provide evaporation condensate, which can be sent back to the mixer as stream 4 and/or utilized in the optional multistage countercurrent wash/separation step 274, and also provide a concentrated sugar stream, which includes C6 and/or C5 sugars and other dissolved solids, that can be further processed, such as via fermentation, for example. In addition, the evaporation condensate may be utilized in the ultrafiltration step 276 as wash/dilution water. In one example, the sugar stream can be subjected to an initial set of three evaporators, as are known in the art, to begin evaporating the liquid portion of the sugar stream, then subjected further to another set of three evaporators whereat the liquid portion is further evaporated therefrom to ultimately yield the more concentrated sugar stream, which may be referred to as a syrup. In one example, the sugar stream may be subjected to evaporation to remove excess liquid to provide a sugar stream that is 30-80% solids. In another example, the sugar stream is 50% or greater solids. In another example, the sugar stream is 70% or greater solids.

From the optional evaporation step 280, in one example, the concentrated sugar stream, or syrup, can be subjected to any biochemical conversion process or similar sugar utilization process, as is known in the art. Other options for the sugar stream, aside from fermentation, can include further processing or refining of, for example, the glucose to fructose or other simple or even complex sugars, processing into feed, microbe-based fermentation (as opposed to yeast-based) and other various biochemical/chemical, pharmaceutical or nutraceutical processing (such as propanol, isobutanol, lactic acid, citric acid or succinic acid) and the like. Such processing can occur via a reactor, which can include a fermenter. In another example, the concentrated sugar stream, or syrup, can be sent to a carbon treatment and/or an ion exchange device to still further purify the sugar stream by removing any anions and/or cations as well as color and other non-sugar molecules. In still another example, the concentrated sugar stream, or syrup, may be further subjected to a nanofiltration step (not shown), similar to the ultrafiltration and microfiltration steps 276, 260, 266, to specifically separate the C5 and C6 sugars and provide separate sugar streams, e.g., separate xylose and glucose sugar streams, which can be utilized as feedstock for further processing into high value biochemicals/chemicals.

With reference now to FIGS. 2 and 2A, a system and method 300 for producing a carbohydrate (e.g., sugar) stream from a cellulosic feedstock in accordance with another embodiment of the invention is shown wherein cellulosic feedstock 202, e.g., brown stock (pulp) feedstock, which has been pretreated (e.g., unwashed, washed, and/or neutralized), or waste fiber sludge, for example, can be sent to a multi-grind step 600 and initially combined with backset liquid and/or water to help create a slurry and attain a desired total solids. It should be appreciated that the system and method 300 is similar to the system and method 200 of FIGS. 1-1C, with the exception that the mixing, dewater, and grinding steps 204, 205, 206 of FIGS. 1 and 1A have been replaced with multi-grind step 600, which can include multiple steps as shown in FIG. 2A and further described hereinbelow. It is noted that like reference numerals are retained in FIGS. 2 and 2A.

With continuing reference to FIGS. 2 and 2A and concerning the multi-grind step 600, cellulosic feedstock 202 is initially provided to a first liquid/solid separation step 610. The liquid/solid separation step 610 separates a generally liquefied solution (about 60-80% by volume), which includes oligosaccharides, disaccharides, enzymes, and other dissolved solids (e.g., ash), as the permeate, from the concentrate or retentate, which includes solids, such as fibers (e.g., lignin, unhydrolyzed cellulose, etc.). The liquid/solid separation step 106 uses dewatering equipment, e.g., a paddle screen, a vibration screen, screen decanter centrifuge or conic screen centrifuge, a pressure screen, a preconcentrator, and the like, to accomplish separation of the solids from the liquid portion. The fine solids are no greater than 1000 microns. In another example, the fine solids are no greater than 600 microns, which is generally dependent upon the screen size openings used in the liquid/solid separation device(s).

In one example, the dewatering equipment is a paddle screen, which includes a stationary cylinder screen with a high speed paddle with rake. The number of paddles on the paddle screen can be in the range of 1 paddle per 4 to 8 inches of screen diameter. In another example, the dewatering equipment is a preconcentrator, which includes a stationary cylinder screen with a low speed screw conveyor. The conveyor pitch on the preconcentrator can be about ⅙ to ½ of the screen diameter. The number of paddles on the paddle screen and the conveyor pitch on the preconcentrator can be modified depending on the amount of solids in the feed. The gap between the paddle screen and paddle can range from about 0.1 to about 5 mm. A smaller gap gives a drier cake with higher capacity and purer fiber but loses more fiber to filtrate. A larger gap gives a wetter cake with lower capacity and purer liquid (less insoluble solid). The paddle speed can range from 200 to 1200 RPM. In another example, the paddle speed can range from 800 to 900 RPM. A higher speed provides higher capacity but consumes more power. One suitable type of paddle screen is the FQ-PS32 paddle screen, which is available from Fluid-Quip, Inc. of Springfield, Ohio.

The screen for the dewatering equipment can include a wedge wire type with slot opening, or a round hole, thin plate screen. The round hole screen can help prevent long fine fiber from going through the screen better than the wedge wire slot opening, but the round hole capacity is lower, so more equipment may be required if using round hole screens. The size of the screen openings can range from about 600 to 800 microns. In another example, the screen openings can range from 200 to 500 microns. In yet another example, the screen openings can range from 25 to 300 microns.

The separated dewatered solids portion of the stream after the liquid/solid separation step 610 (about 60 to 65% water) is next subjected to a first dewatered milling step 612. The solids, particularly the fibers (e.g., lignin, unhydrolyzed cellulose, etc.), are reduced in size via size reduction equipment, which breaks the biomass and exposes more surface area of the solids to enzymatic hydrolysis. The size reduction equipment can include a hammer mill, a pin or impact mill, a grind mill, a flaking mill, a bauer mill, roller mill, and the like. In one example, the size reduction equipment is a pin mill or grind mill. One type of grind mill having a suitable type of grind plate is the FQ-136 or FQ-152 grind mill, which are available from Fluid-Quip, Inc. of Springfield, Ohio. One suitable type of pin/impact mill is the FQ-IM40, which is available from Fluid-Quip, Inc. of Springfield, Ohio.

In a dewatered form, the solids are able to break apart more easily as a result of increased rubbing action. This results in a relatively non-uniform particle size amongst the milled solids. For example, cellulosic solids can be milled to a particle size between about 1000 to 1500 microns, whereas a majority of the solids, including the fiber, can remain within a particle size range of 800 to 1200 microns. In one example, greater than 75% of the fiber remains within a particle size range of 500 to 800 microns. In another example, no greater than 80% by weight of the total particles after the dewatered milling step 612 have a particle size less than 1000 microns. In another example, about 30% to about 50% by weight of the total particles after the dewatered milling step 612 have a particle size from about 500 microns to about 800 microns. It is contemplated that other ranges of total particle size can be achieved from about 250 micron to greater than 3000 micron. It is understood that the range of particles can be dependent upon the type of starting cellulosic material (feedstock). Various additional enzymes (and types thereof) can be optionally added to enhance the separation of components, such as to help break the bonds between protein, starch, lignin, and fiber.

The heavy slurry from the dewatered milling step 612 is sent to a first holding tank step 614 whereat the heavy slurry can recombine with the separated liquid portion from the first liquid/solid separation step 610. Additionally, liquid portions from downstream optional liquid/solid separation steps 616 and 622 may be recycled and introduced back into the first holding tank 614, thereby facilitating greater fluid flow of the relatively thick slurry.

At first holding tank 614, the recombined stream next can be sent directly to sugar conversion step 258 or, as shown, subjected to optional second and third liquid/solid separation step 616, 622, which uses dewatering equipment, e.g., a paddle screen, a vibration screen, screen decanter centrifuge or conic screen centrifuge, a disc nozzle centrifuge, a pressure screen, a preconcentrator, and the like, to accomplish separation of the solids from the liquid portion like the first liquid/solid separation step 610, followed by optional and corresponding second and third dewatered milling steps 618, 624 and second and third holding tanks 620, 626. The optional liquid/solid separation steps 616, 622 separate a generally liquefied solution (about 60-80% by volume), which includes oligosaccharides, disaccharides, enzymes, and other dissolved solids (e.g., ash), as the permeate, from the concentrate or retentate, which includes solids, such as fibers (e.g., lignin, unhydrolyzed cellulose, etc.). And at each of the optional second and third dewatered milling steps 618, 624, the separated solids, particularly the fibers (e.g., lignin, unhydrolyzed cellulose, etc.), are further reduced in size via size reduction equipment, which breaks the biomass and exposes more surface area of the solids to enzymatic hydrolysis. Finally, the heavy slurry from the optional dewatered milling steps 618, 624 are sent to corresponding second and third holding tanks 620, 626 whereat the heavy slurry can recombine with the separated liquid portion from the second and third liquid/solid separation steps 616, 622, respectively. While two additional optional liquid/solid separation steps, dewatered milling steps, and holding tanks are shown here, it should be understood that this number is not limiting such that more than or less than shown may be utilized.

The recombined stream at the third holding tank 626 can be sent directly to sugar conversion step 258 for further processing of the stream as discussed above with respect to FIGS. 1-1C. Throughout the multi-grind process 600, and to prolong the viability of the enzyme activity of the entire process, again the average bulk fluid temperature is carefully controlled. For example, the heavy slurry transferred from the first dewatered milling step 612 is pumped or transferred to the first holding tank 614 and held for a residence time of about 1 to 3 hours at a temperature of about 30° C. to 70° C., and more preferably at about 40-60° C., and even more preferably at about 50° C. Similar process parameters may be followed for additional optional separation and milling steps and holding tanks. In other examples, the temperature of the first holding tank 614 can be greater than or less than 50° C. insofar as the temperature can be dependent upon the temperature needed for optimal enzyme activity. And filtrate from subsequent second liquid/solid separation and second dewatered milling steps 616 and 618, and third liquid/solid separation and third dewatered milling steps, for example, may be similar to the filtrate from the first solid/separation and first dewatered milling steps 610 and 612, respectively, and may be recycled back in a counter current set up to mix with milled solids after the first and second dewatered milling steps 612 and 618 to form a heavy slurry. Again, this heavy slurry is sent to the first, second, and/or third holding tanks, 614, 620, and/or 626 respectively and preferably held for about 1 to 3 hours at a temperature of about 30° C. to 70° C., and more preferably at about 40-60° C., and even more preferably at about 50° C., before finally being transferred to the sugar conversion step 258.

With this system and method 200, 300, it is understood that the life-expectancy or operational efficacy of the enzyme(s) used can be up to two times (or more) than that of known single pass processes, and perhaps even up to ten times that of known single pass processes, thereby realizing substantial savings in capital, operational, and system expenses. The use of recycled enzymes in the feedstock is understood to accelerate the normal reaction time, thereby compressing the time normally needed to provide a given unit of bio-mass. The present invention also can provide greater purification of pulp and paper products that would typically be burned or otherwise disposed of. Here, the enhanced purity of lignin, for example, may be used to produce high-value chemicals, for example.

While the present invention has been illustrated by a description of various embodiments and while these embodiments have been described in considerable detail, it is not the intention of the applicant to restrict or in any way limit the scope of the appended claims to such detail. The apparatuses/devices and/or steps discussed above with respect to the system and method 200, 300 may include multiples of the same apparatus and/or step, in series and/or parallel or in sequence, as desired or necessary therefore. In addition, adjustments to temperature, pH, residence time, etc. may be made, as needed or desired, at the various steps throughout the system and method 200, 300 including at the mixer 204, etc., such as to optimize the use of enzymes and/or chemistries. Additional advantages and modifications will readily appear to those skilled in the art. Thus, the invention in its broader aspects is therefore not limited to the specific details, representative apparatus and method and illustrative example shown and described. Accordingly, departures may be made from such details without departing from the spirit or scope of applicant's general inventive concept.

What is claimed is:

1. A method for producing a carbohydrate stream from a cellulosic feedstock comprising:
   mixing a cellulosic feedstock with at least one enzyme and a liquid to produce a slurry and begin enzymatic hydrolysis of the cellulosic feedstock; wherein the at least one enzyme is selected from endoglucanase, cellulase, β-glucanase, xylonase, or hemicellulase
   subjecting the slurry to a carbohydrate conversion step to further hydrolyze the cellulosic feedstock in the slurry from oligosaccharides and/or disaccharides to C5 and/or C6 simple sugars and produce a stream including the C5 and/or C6 simple sugars, the at least one enzyme, and unhydrolyzable components;
   after the carbohydrate conversion step but prior to further processing of the C5 and/or C6 simple sugars, separating the stream into a solids portion including the unhydrolyzable components and a liquid portion including the C5 and/or C6 simple sugars and the at least one enzyme, wherein the liquid portion defines a carbohydrate stream where at least 50% of total sugar in that stream is the C5 and/or C6 simple sugars and/or where the total unhydrolyzable solids fraction of the stream is less than or equal to 30% of the total solids content; and
   separating the at least one enzyme from the liquid portion.

2. The method of claim 1 further comprising recovering the carbohydrate stream.

3. The method of claim 1 further comprising recycling the separated enzyme to a step earlier in the method for reuse.

4. The method of claim 3 wherein separating the at least one enzyme from the liquid portion comprises subjecting the liquid portion to a filtration step to produce a permeate including the C5 and/or C6 simple sugars and a retentate including the at least one enzyme, and recycling the separated enzyme in the permeate to a step earlier in the method for reuse.

5. The method of claim 4 wherein the filtration step is an ultrafiltration step.

6. The method of claim 3 wherein mixing the cellulosic feedstock comprises mixing the cellulosic feedstock with the at least one enzyme, which includes the separated enzyme, and the liquid to produce a slurry and begin enzymatic hydrolysis of the cellulosic feedstock.

7. The method of claim 1 further comprising subjecting the carbohydrate stream to a carbohydrate utilization process to produce a biochemical.

8. The method of claim 7 wherein the biochemical is a biofuel.

9. The method of claim 7 wherein the carbohydrate utilization process is fermentation to produce a biochemical.

10. The method of claim 1 wherein the cellulosic feedstock is non-food biomass feedstock.

11. The method of claim 10 wherein the non-food biomass feedstock is pretreated brown stock feedstock.

12. The method of claim 1 further comprising, after mixing the cellulosic feedstock, grinding the slurry followed by subjecting the slurry to the carbohydrate conversion step.

13. The method of claim 1 wherein mixing the cellulosic feedstock comprises mixing a cellulosic feedstock with recovered C5 and/or C6 simple sugars from a step later in the method, the at least one enzyme, and the liquid to produce a slurry and begin enzymatic hydrolysis of the cellulosic feedstock to C5 and/or C6 simple sugars.

14. The method of claim 1 wherein mixing the cellulosic feedstock comprises mixing a cellulosic feedstock with neutralized recalcitrant fiber from a step later in the method, the at least one enzyme, and the liquid to produce a slurry and begin enzymatic hydrolysis of the cellulosic feedstock to simple sugars.

15. The method of claim 1 wherein the liquid portion defines a carbohydrate stream where at least 90% of the total sugar in that stream is the C5 and/or C6 simple sugar and/or where the total unhydrolyzable solids fraction of the stream is less than or equal to 5% of the total solids content.

16. The method of claim 1 wherein, after the carbohydrate conversion step but prior to further processing of the simple sugars, separating the stream comprises separating the stream, via microfiltration, into the solids portion including the unhydrolyzable components and the liquid portion including the C5 and/or C6 simple sugars and the at least one enzyme.

17. The method of claim 1 further comprising subjecting the solids portion including the unhydrolyzable components to a multi-stage countercurrent wash and separation process.

18. The method of claim 1 further comprising subjecting the solids portion including the unhydrolyzable components to acid hydrolysis or caustic solubilization.

19. The method of claim 1 wherein the liquid in the mixing step comprises water and/or backset liquid from a step later in the method.

20. The method of claim 1 wherein the carbohydrate stream defines a sugar stream and further comprising recovering the sugar stream.

\* \* \* \* \*

UNITED STATES PATENT AND TRADEMARK OFFICE
CERTIFICATE OF CORRECTION

PATENT NO. : 10,995,351 B1
APPLICATION NO. : 17/019696
DATED : May 4, 2021
INVENTOR(S) : Robert et al.

Page 1 of 1

It is certified that error appears in the above-identified patent and that said Letters Patent is hereby corrected as shown below:

In the Claims

Column 25, Line 66, Claim 1, "hydrolysis of the cellulosic feedstock; wherein the at" should be
-- hydrolysis of the cellulosic feedstock, wherein the at --

Signed and Sealed this
Sixth Day of July, 2021

Drew Hirshfeld
*Performing the Functions and Duties of the
Under Secretary of Commerce for Intellectual Property and
Director of the United States Patent and Trademark Office*